(12) United States Patent
Ariura et al.

(10) Patent No.: US 7,022,118 B2
(45) Date of Patent: Apr. 4, 2006

(54) MEDICAL ENERGY IRRADIATION APPARATUS

(75) Inventors: Shigeki Ariura, Nakai-machi (JP); Akira Sakaguchi, Nakai-machi (JP); Shin Maki, Nakai-machi (JP)

(73) Assignee: Terumo Kabushiki Kaisha, Tokyo (JP)

( * ) Notice: Subject to any disclaimer, the term of this patent is extended or adjusted under 35 U.S.C. 154(b) by 10 days.

(21) Appl. No.: 10/180,291

(22) Filed: Jun. 27, 2002

(65) Prior Publication Data

US 2003/0004417 A1    Jan. 2, 2003

(30) Foreign Application Priority Data

Jun. 29, 2001  (JP) .............................. 2001-199535

(51) Int. Cl.
 *A61B 18/20*   (2006.01)
(52) U.S. Cl. .................. 606/10; 606/17; 606/18; 600/108
(58) Field of Classification Search .................. 606/6, 606/10–15; 600/108
See application file for complete search history.

(56) References Cited

U.S. PATENT DOCUMENTS

| | | | |
|---|---|---|---|
| 4,211,229 A | 7/1980 | Wurster | |
| 4,445,892 A | 5/1984 | Hussein et al. | |
| 4,667,655 A | 5/1987 | Ogiu et al. | |
| 4,672,963 A | 6/1987 | Barken | |
| 4,760,840 A | 8/1988 | Fournier, Jr. et al. | |
| 4,773,413 A | 9/1988 | Hussein et al. | |
| 4,932,956 A | 6/1990 | Reddy et al. | |
| 4,932,958 A | 6/1990 | Reddy et al. | |
| 5,049,147 A | 9/1991 | Danon | |
| 5,207,672 A | 5/1993 | Roth et al. | |
| 5,248,311 A | 9/1993 | Black et al. | |
| 5,292,320 A | 3/1994 | Brown et al. | |
| 5,350,375 A | 9/1994 | Deckelbaum et al. | |
| 5,421,323 A * | 6/1995 | Herrmann et al. | 600/170 |
| 5,450,846 A | 9/1995 | Goldreyer | |
| 5,496,308 A | 3/1996 | Brown et al. | |
| 5,769,843 A | 6/1998 | Abela et al. | |
| 5,827,312 A * | 10/1998 | Brown et al. | 606/79 |
| 6,117,071 A | 9/2000 | Ito et al. | |
| 6,171,303 B1 | 1/2001 | Ben-Haim et al. | |

(Continued)

FOREIGN PATENT DOCUMENTS

| | | |
|---|---|---|
| EP | 0 673 627 A1 | 9/1995 |
| EP | 0 815 895 A1 | 1/1998 |

(Continued)

*Primary Examiner*—David M. Shay
(74) *Attorney, Agent, or Firm*—Buchanan Ingersoll PC

(57) ABSTRACT

To provide a medical energy irradiation apparatus which permits easy and accurate establishment of a site of tissues of a living body targeted for irradiation with energy, when doctors use the medical energy irradiation apparatus to perform a cure for a prostatic hyperplasia or the like. The doctors insert an applicator 110 of the medical energy irradiation apparatus to an urinary bladder 161 and fix an endoscope 135 near to an entrance of an urethra. In this arrangement, when observing with the endoscope (135), a seminal colliculas 144 observed through a side-observation window 130 is observed toward a lower part of an observed image (schematic diagram) displayed on a display unit, and a positioning marker 140 in an interior of the applicator is observed toward an upper part of an observed image. The doctors can accurately determine a position to be irradiated with laser light from positions of the seminal colliculas 144 and the positioning marker 140 observed, and a direction of irradiation with laser light from a position of a direction marker 142, respectively.

11 Claims, 20 Drawing Sheets

U.S. PATENT DOCUMENTS

| | | |
|---|---|---|
| 6,321,109 B1 | 11/2001 | Ben-Haim et al. |
| 6,379,347 B1 * | 4/2002 | Maki et al. ................... 606/17 |
| 6,530,921 B1 * | 3/2003 | Maki ........................... 606/15 |
| 6,544,257 B1 * | 4/2003 | Nagase et al. ............... 606/15 |
| 6,579,286 B1 * | 6/2003 | Maki et al. ................... 606/17 |
| 6,599,287 B1 * | 7/2003 | Iwahashi et al. ............. 606/14 |
| 6,607,526 B1 * | 8/2003 | Maki ........................... 606/16 |
| 2001/0053907 A1 | 12/2001 | Ota |

FOREIGN PATENT DOCUMENTS

| | | | | |
|---|---|---|---|---|
| EP | 1 075 822 A2 | | 2/2001 | |
| JP | 11-276606 | * | 10/1999 | ................ 600/108 |
| JP | 2001-145630 A | | 5/2001 | |
| WO | WO 92/04934 A1 | | 4/1992 | |
| WO | WO 93/04727 A1 | | 3/1993 | |
| WO | 9315664 | * | 8/1993 | ................ 606/15 |
| WO | WO 00/74565 A1 | | 12/2000 | |

* cited by examiner

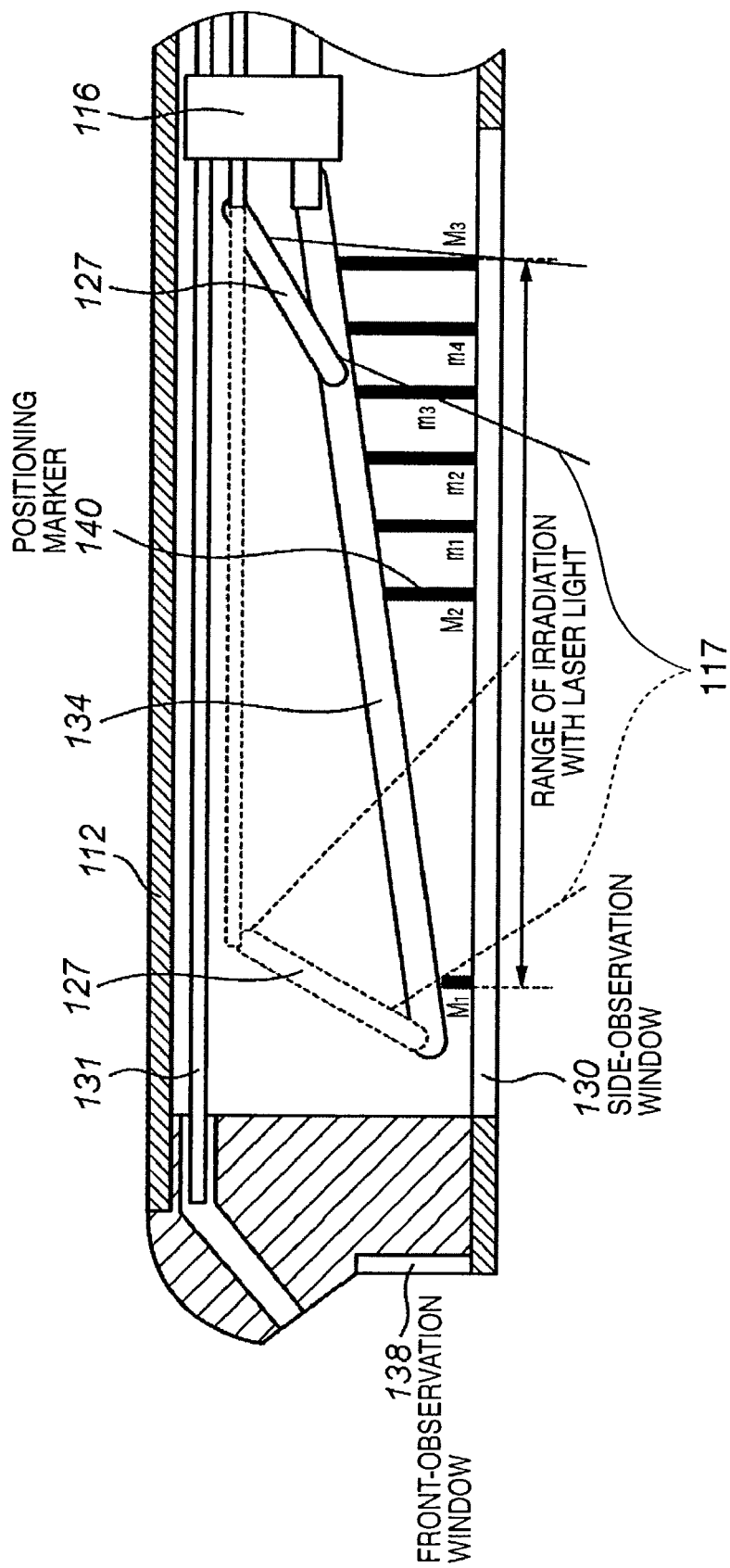

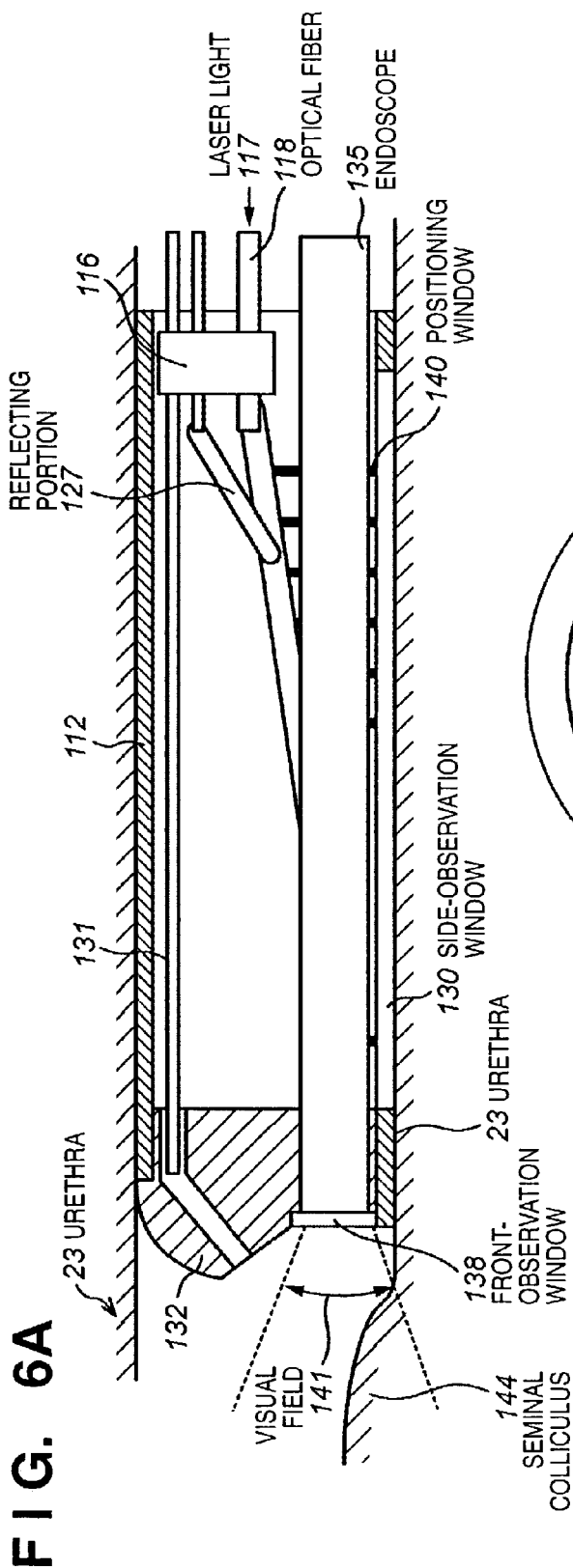
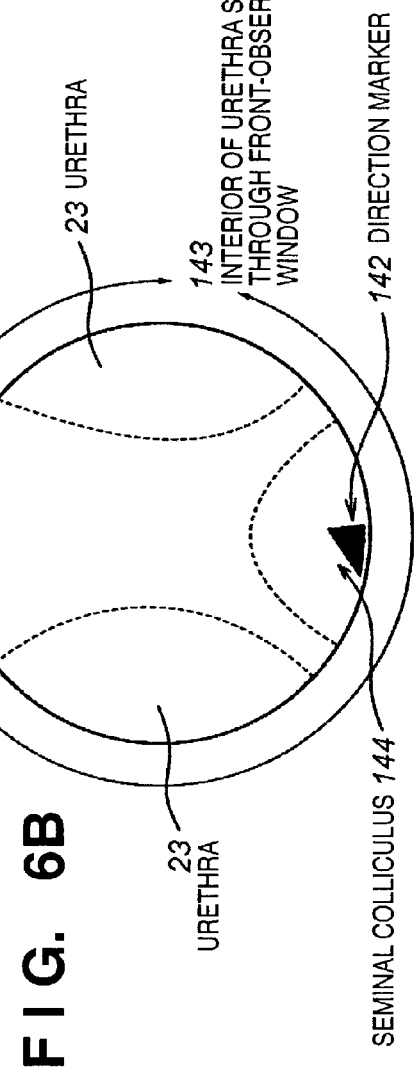
FIG. 6A
FIG. 6B

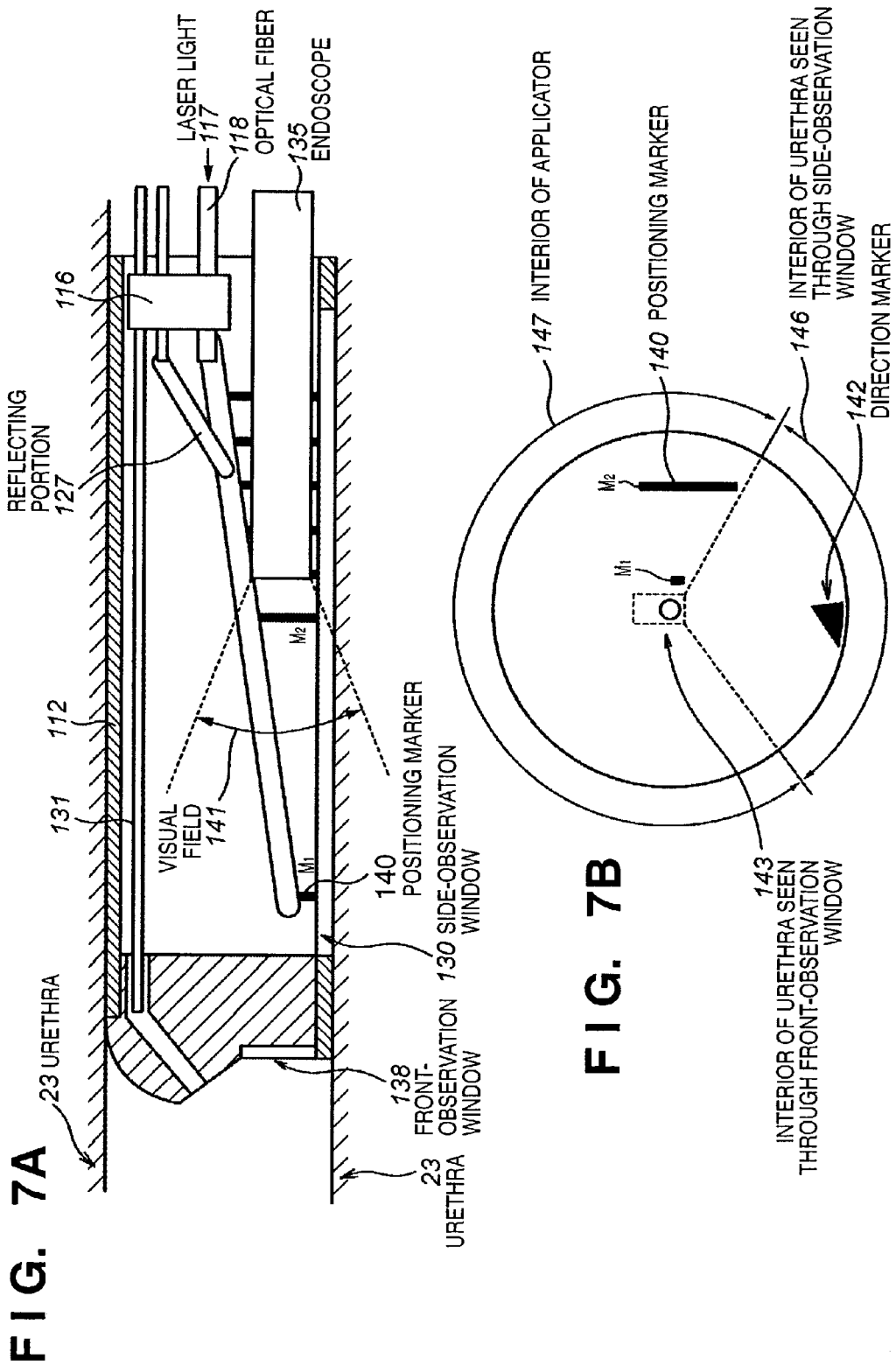

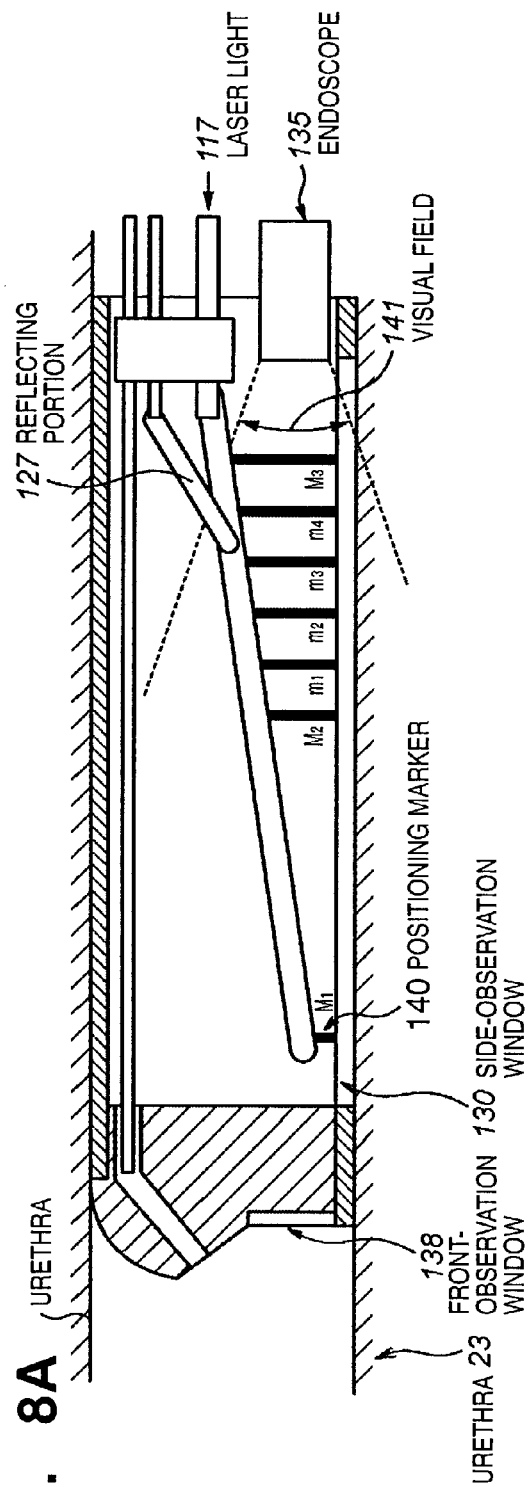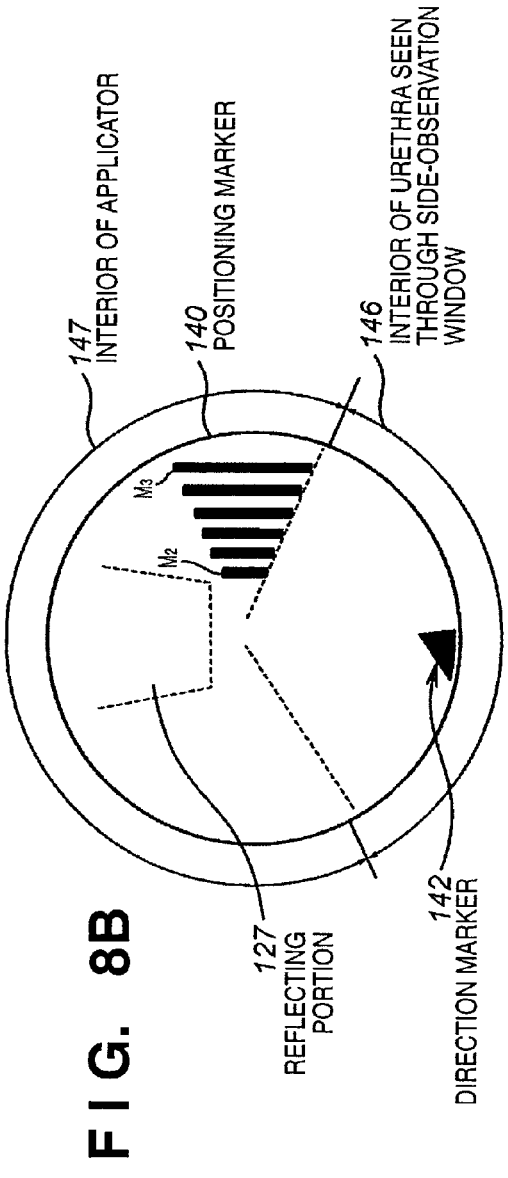
FIG. 8A
FIG. 8B

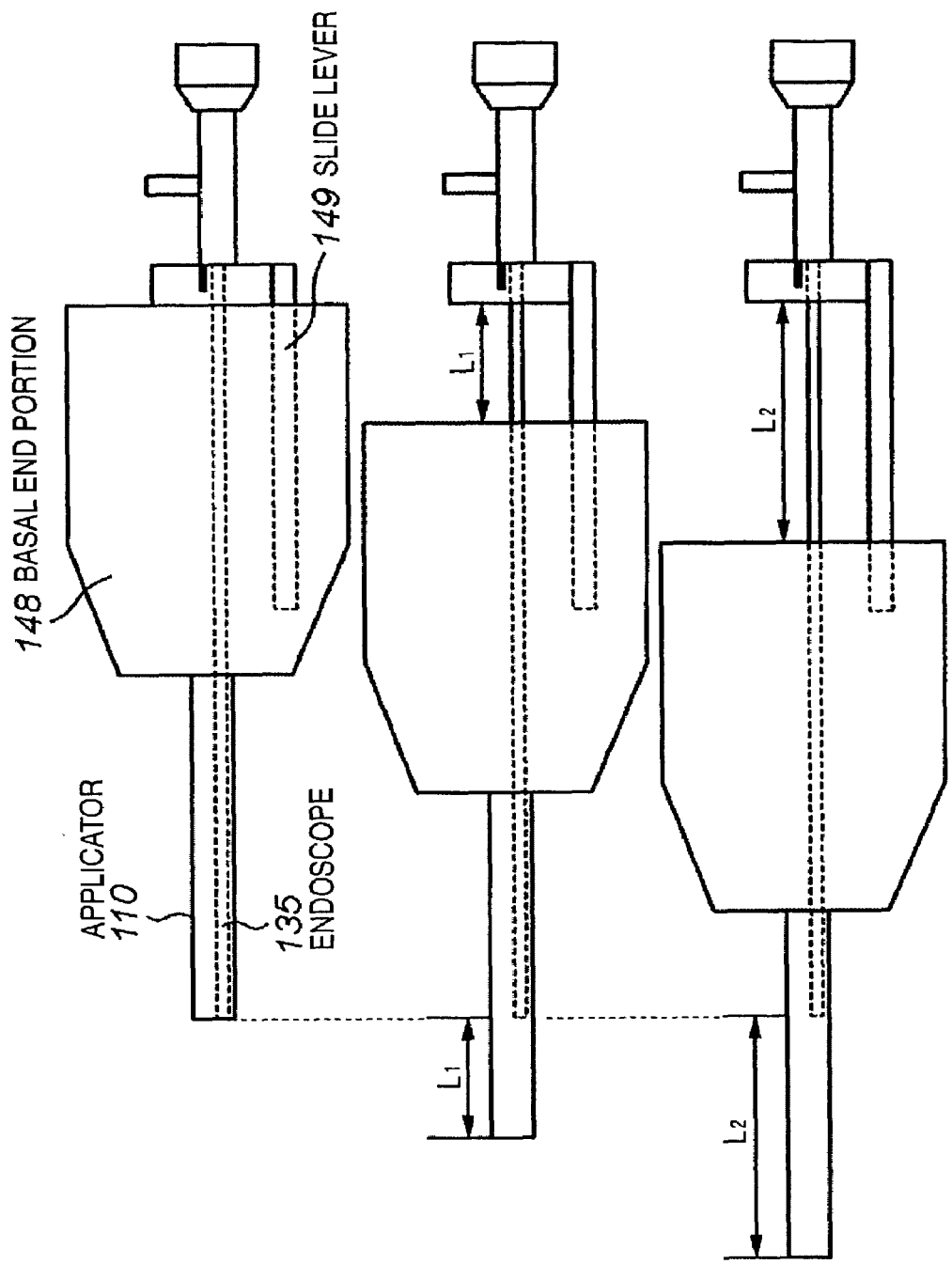

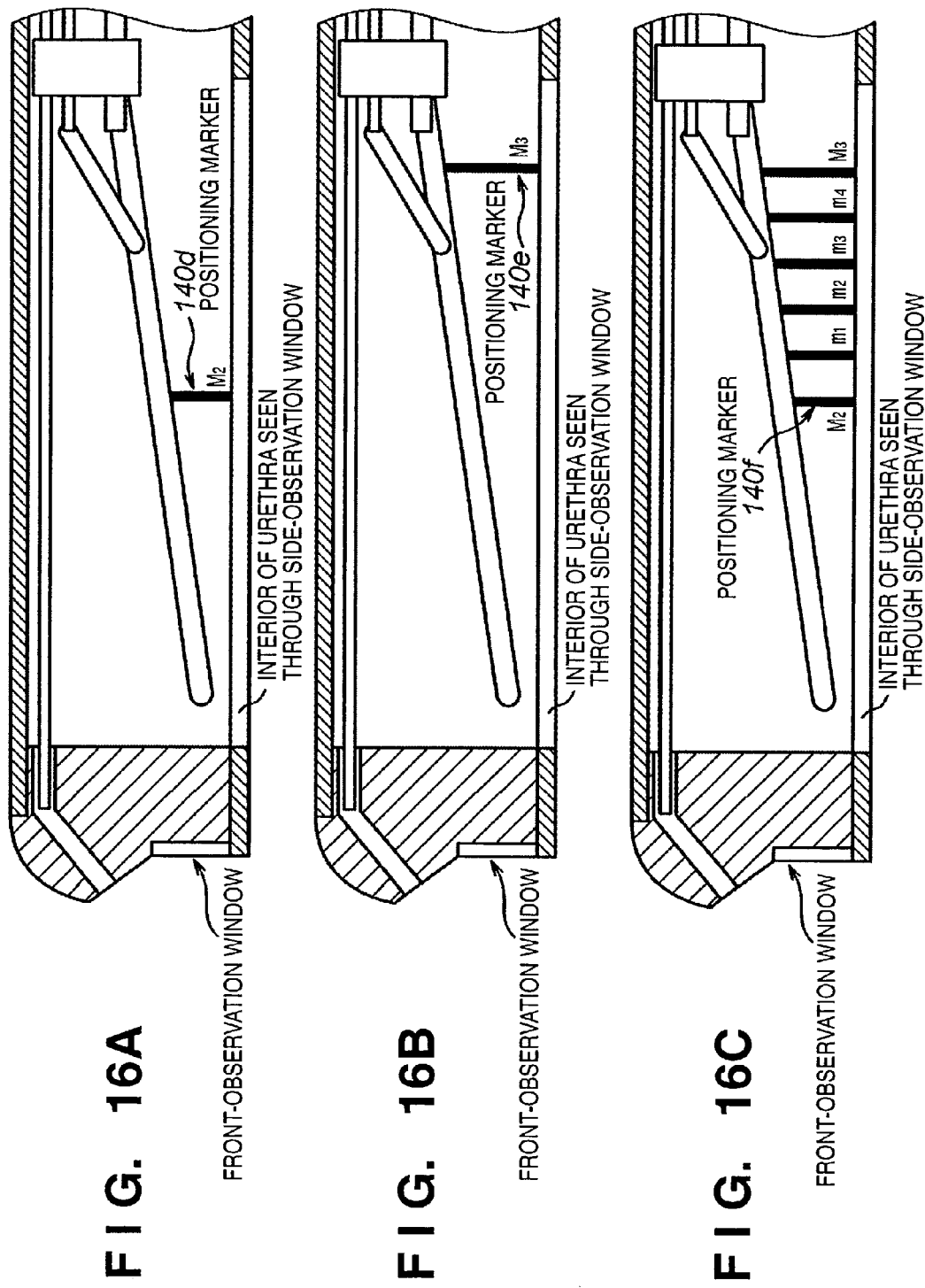

ANGLE DENOTATION SHEET

MEDICAL ENERGY IRRADIATION APPARATUS

FIELD OF THE INVENTION

The invention relates to a medical energy irradiation apparatus inserting an inserting portion thereof into a cavity or a lumen in a living body, such as a blood vessel, gastrointestinal tract, urinary tract, abdominal cavity, thoracic cavity, and irradiating tissues of a living body with energy, such as laser light, a microwave, radio frequency, and ultrasonic wave, from an emitting portion provided in the inserting portion to perform a cure for the tissues of a living body including a lesion. Further, it relates to a medical energy irradiation apparatus which permits easy and accurate establishment of a target position to be irradiated with the energy, in heat-curing for only a target depth of the living body, for example, a tumor, such as a cancer, and prostatic hyperplasia.

BACKGROUND OF THE INVENTION

There is known a medical energy irradiation apparatus which inserts an inserting portion thereof shaped like a longer measure into a living body by using a body cavity or performing small incision, and irradiates the tissue of a living body including a lesion with energy, such as laser light, a microwave, radio frequency, and ultrasonic wave, from this inserting portion, thereby destroying the tissue of the lesion by degeneration, necrosis, coagulation, ablation or vaporization.

The medical energy irradiation apparatus is generally for performing a cure by applying direct irradiation with energy to a lesion located on a surface of a tissue of a living body or in the proximity thereof. However, it is also applied to heat-curing for a lesion located in a deep part of a tissue of a living body, such as a prostate gland. Also, there is known a medical energy irradiation apparatus that is configured to be cooled with coolant in the proximity of its energy emitting portion provided in the inserting portion. According to this energy irradiation apparatus, because a tissue of a living body making contact with the energy emitting portion or the neighborhood thereof is cooled in the surface or in the proximity thereof, these parts can be protected from heat-injury and only a deep part of the tissue of a living body can be heated intensively.

When, for example, a cure for a prostate gland is performed by using this medical energy irradiation apparatus, generally the following procedures are performed. That is, the doctors performing a cure for a prostate gland first insert the inserting portion of the medical energy irradiation apparatus toward the urinary bladder from the urethra of patients, and make the emitting portion reach to a portion of the urethra enclosed by the prostate gland (prostatic urethra). Then, in that position, the doctors align the position of the emitting portion to the direction of a target site in the urethra, thus performing irradiation with energy. The doctors generally perform this series of operations while they are observing the views of each position in the urethra by an endoscope that can be inserted in the longitudinal direction.

To describe one example of the above described alignment of the emitting portion in detail, the doctors first insert a predetermined length of the inserting portion of the medical energy irradiation apparatus from the urethra entrance of the patients, and fix the inserting section and the endoscope at this position, and then observe and store the view of the proximal end portion of the urethra irradiated with energy observed by the endoscope in memory. Next, the doctors further insert the endoscope toward a deeper part in the direction of the urinary bladder of the patients by a predetermined length with the inserting section fixed in the urethra, and fix the endoscope at the position, and then again observe and store the view of the distal end portion of the urethra irradiated with energy therein observed by the endoscope in memory.

The doctors repeatedly carry out the above described operations of the endoscope while changing the position of the inserting section to be fixed in the urethra, thereby positioning the emitting portion toward a target position, that is, a target position for irradiating a target site with energy. Also, when the doctors judge that the endoscope has been inserted beyond the target position, they return the inserting section toward the urethra entrance and fix it, and the doctors repeatedly carry out the series of operations of the endoscope, as well, to move the inserting section to the target position, and fix if therein. Further, the doctors have determined a position for fixing the point of the inserting section based on a distance from the seminal colliculus in the urethra to be observed by an endoscope.

Also, when the doctors perform the heat-curing using the medical energy irradiation apparatus described above at a plurality of positions, they repeatedly perform the above described operations for each of the positions.

However, according to the above described method, the doctors determine an irradiation target position for heat-curing by visual observation while they are moving the endoscope. For this reason, although the doctors can roughly grasp the target position, it has been impossible to determine reliably and accurately the portion for fixing the inserting section thereto.

Also, in performing heat-curing by the medical energy irradiation apparatus described above, when the doctors place the emitting portion at an appropriate irradiation target position in a urethra surrounded by a prostate gland, they have sometimes placed the emitting portion at a position closer to the urinary bladder beyond the appropriate irradiation target position in the urethra, or sometimes placed it on the side of external urethral sphincter located at the front of the appropriate irradiation target position in the urethra.

In this way, when the doctors fail to place the inserting portion of the medical energy irradiation apparatus on an appropriate position of placement, the patients cannot obtain a sufficient heat cure effect or can be damaged in the healthy urinary bladder or external urethral sphincter thereof.

Also, when the heat-curing by the medical energy irradiation apparatus described above is performed a plurality of times, the possibility of error operations as described above further increase, because the doctors must perform the operation of positioning the inserting portion a plurality of times.

Also, when the heat-curing is performed by using a medical energy irradiation apparatus provided with an emitting portion having a wide range of energy irradiation, it is difficult for the doctors to limit the range of energy irradiation only to the prostate gland of the irradiation target site. For this reason, the doctors must irradiate accurately the central portion of the prostate gland with energy, but the conventional methods of setting an energy irradiation target position rely on the guesswork of the doctors in some part. Therefore, it has been impossible to avoid errors occurring in determination of an irradiation target position. For this reason, because of deviation from an energy irradiation target position, there have been fears that the patients cannot obtain a sufficient effect of curing or can be damaged in the healthy urinary bladder or external urethral sphincter.

Furthermore, if the patients feel physical disorder caused by the insertion of the inserting portion into them during heat-curing, searing heat due to heat-curing, and pains, and they move by a reflex action, and even though the doctor realize a deviation in the position of placement, the doctors cannot return the inserting portion to the position of placement prior to the position deviation. As a result, there have been fears that the patients cannot obtain a sufficient effect of curing or can be damaged in the healthy urinary bladder or external urethral sphincter.

SUMMARY OF THE INVENTION

The present invention has been achieved to overcome the above described problems of conventional technologies. An object of the invention is to provide a medical energy irradiation apparatus, which permits easy and accurate establishment of a position targeted for energy irradiation (a site to be irradiated with energy in tissues of a living body), when doctors use the medical energy irradiation apparatus to perform a cure for prostatic hyperplasia or the like.

In order to attain the above object, a medical energy irradiation apparatus according to one embodiment of the invention has the following configurations. That is, a medical energy irradiation apparatus having energy generating means for generating energy, and irradiating tissues of a living body with the above described energy from an emitting portion provided in the interior of an inserting portion which is inserted into the living body, characterized by having an endoscope insertable along the length of the interior of the above described inserting portion, and a position mark provided in the interior of the above described inserting portion for specifying the relative positions of the above described endoscope and the above described inserting portion.

Herein, for example, the apparatus preferably has further emitting portion moving means for moving the above described emitting portion along the length of the above described inserting portion, and emission angle-changing means for changing an emission angle of the above described emitting portion.

Herein, for example, the above described inserting portion preferably has a front-observation window for permitting observation of tissues of a living body existing in front of the above described inserting portion.

Herein, for example, the above described inserting portion preferably has an irradiation window for irradiating a side portion of the above described inserting portion close to the above described front-observation window with the above described energy.

Herein, for example, the above described front-observation window and the above described irradiation window are preferably arranged to have the shortest distance less than 10 mm therebetween.

Herein, for example, the apparatus preferably has endoscope moving means for moving the above described endoscope from the entering portion of the above described inserting portion near to the above described observation window.

Herein, for example, the above described position mark is preferably a marker and provided more than one in number.

Herein, for example, the above described position mark is preferably arranged in the interior of the above described inserting portion.

Herein, for example, the above described position mark is arranged at the position to indicate a limit point of movement of the above described emitting portion.

Herein, for example, the above described endoscope preferably has further an irradiation direction-identifying mark for pointing the direction of irradiation with the above described energy.

Herein, for example, when the above described endoscope is rotated about the longitudinal axis of the above described inserting portion, the above described endoscope preferably has further a rotation angle-identifying mark for permitting identification of rotation direction and rotation angle of the rotation.

Herein, for example, the above described endoscope preferably has further image pickup means for picking up the above described tissues of a living body and the above described position mark, and display means for displaying the image picked up by the above described image pickup means.

Herein, for example, the above described energy is laser light.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

FIG. 5 is a diagram for showing one example in which a positioning marker is provided in an interior of an applicator according to one embodiment of the invention (both ends of the positioning marker indicate the limit points of irradiation with the laser light).

FIG. 6A is a diagram for showing the case where an applicator 110 according to one embodiment of the invention is inserted in a urethra 23 and an endoscope 135 is inserted up to a front end of the applicator 110, and FIG. 6B is a diagram for showing an example of a tissue site of a living body observed by the endoscope 135 of FIG. 6A.

FIG. 7A is a diagram for showing the case where the applicator 110 according to one embodiment of the invention is inserted in the urethra 23 and the endoscope 135 is inserted near to a central portion of the applicator 110, and FIG. 7B is a diagram showing an example of a tissue site of a living body observed by the endoscope 135 of FIG. 7A.

FIG. 8A is a diagram for showing the case where the applicator 110 according to one embodiment of the invention is inserted in the urethra 23 and the endoscope 135 is inserted at a basal end of the applicator 110, and FIG. 8B is a diagram showing an example of the tissue site of a living body observed by the endoscope 135 of FIG. 8A.

FIGS. 9A–9C are diagrams for illustrating a movement mechanism for the endoscope according to one embodiment of the invention.

FIG. 5 and FIG. 15B are the same.

FIGS. 16A–16C are diagrams in which the positioning markers of different kinds from that of FIG. 5 are arranged in the interior of the applicator according to one embodiment of the invention.

DETAILED DESCRIPTION OF THE PREFERRED EMBODIMENTS

Preferred embodiments of the present invention will now be described in detail in accordance with the accompanying drawings.

By the way, in the description below, laser light is used as an example of energy used for heat curing of the prostatic hypertropy or the like, but the energy used for the heat curing does not need to be limited to laser light, and, for example, a microwave, radio frequency, ultrasonic wave, or the like may be used instead of laser light. Also, as an example of the application of a medical energy irradiation apparatus according to the present embodiment, its use for heat curing of the prostatic hyperplasia will be described. However, the application of the medical energy irradiation apparatus according to the present embodiment is not limited to heat curing of the prostatic hyperplasia, and can be used for heating curing of tumors such as cancer or the like.

Figure 1:
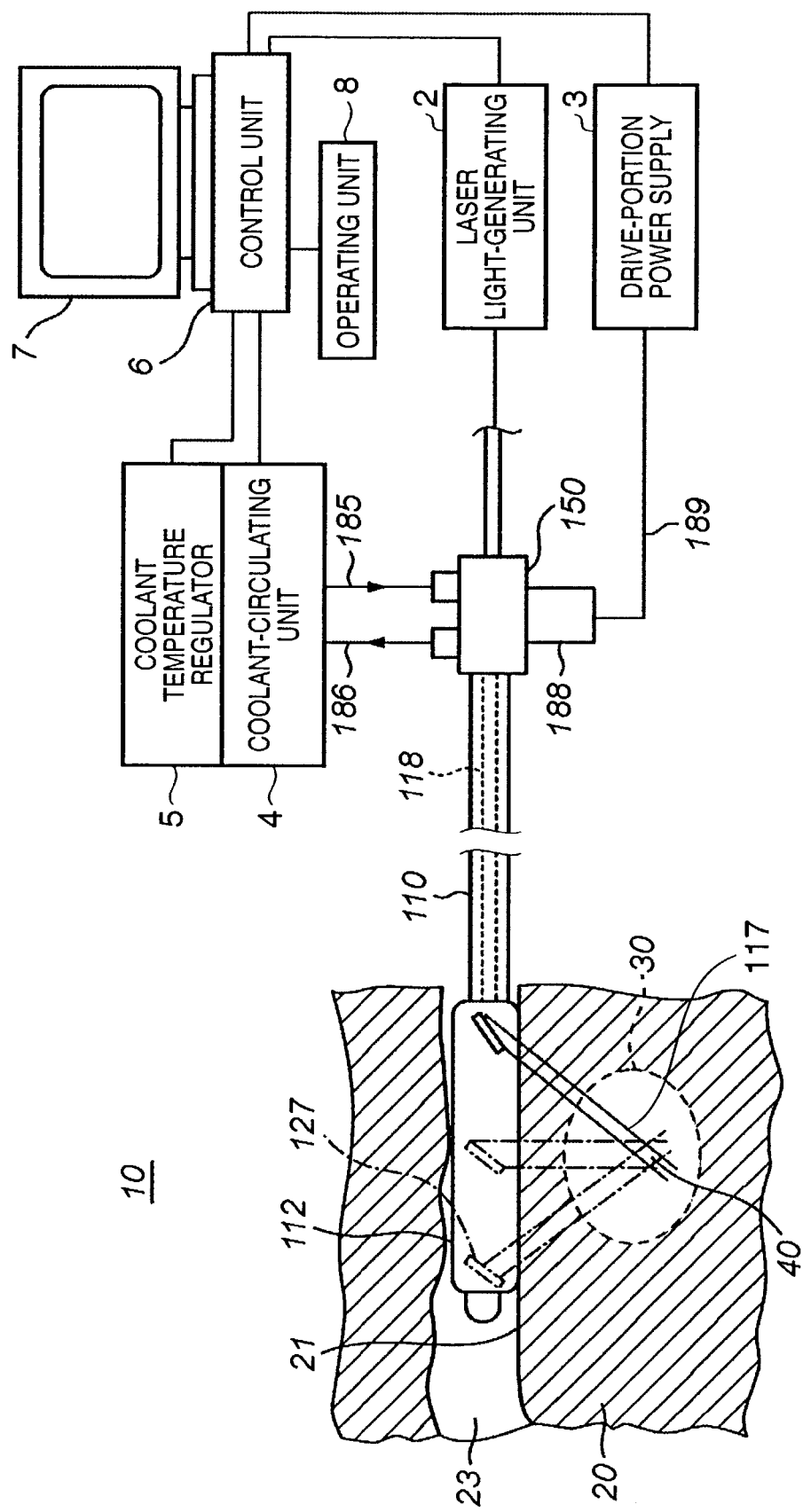
FIG. 1 is a system block diagram of a medical energy irradiation apparatus according to one embodiment of the invention.

[Medical Energy Irradiation Apparatus: FIG. 1]

FIG. 1 is a system block diagram of a medical energy irradiation apparatus 10 for heat curing of a prostatic hyperplasia according to the present invention.

The medical energy irradiation apparatus 10 has an applicator 110 for laser-light irradiation of a sideward-irradiating type, which applicator is inserted into a living body (for example, a urethra 23), and irradiation with laser light 117 guided from a laser light generating unit 2 through an optical fiber 118 is performed toward a tissue of a living body 20 from a housing 112.

Further, the applicator 110 for laser irradiation is provided with a plurality of coolant-circulating lumens (not shown) which communicate with the housing 112 connected to the tip portion of the applicator. These lumens are connected with a coolant-sending tube 185 and a coolant return tube 186 of a coolant-circulating unit 4.

The coolant-circulating unit 4 sends out a coolant at a predetermined flow rate to the laser-light irradiation applicator 110 based on a control signal from a control unit 6. A coolant temperature regulator 5 performs temperature control of the coolant by heating or cooling it based on a control signal from the control unit 6. A motor 188 rotates in a predetermined number of revolutions based on a control signal from the control unit 6.

The control unit 6 comprises an operation unit (8) as input means, a display unit 7 for displaying input information and apparatus information, a controller (not shown) for controlling each device, a memory unit (not shown) for various information, and an input and output unit (not shown) for various information.

During heat curing of an irradiation target site of a prostate gland (target point) 40 by a laser beam, a coolant is supplied from the coolant-circulating unit 4 to the laser-light irradiation applicator 110 through the coolant-sending tube 185, and the motor 188 rotates, and the laser-light generating unit 2 is operated.

The generated laser light 117 is guided to the front end of the laser-light irradiation applicator 110, reflected by a reflecting portion 127, and passes through a window portion, thus the irradiation target site (target point) 40 being irradiated with the laser light. At this time, the reflecting portion 127 changes its irradiation angles while performing an reciprocating motion in the axial direction with cycles 2–10 Hz, preferably 3–6 Hz. However, because all the optical paths of the laser light 117 cross each other at the irradiation target site (target point) 40 of the prostate gland (target position) 30, the irradiation target site (target point) 40 is continuously subjected to irradiation with the laser light 117 to absorb a large amount of heat, thus heated to a high temperature.

On the other hand, on the surface 21 of the tissue of the living body 20 (that is, the neighborhood of the surface of the urethra), the positions irradiated with the laser light 117, of which irradiation angles is being changed by the axial reciprocating motion of the reflection plane 127, constantly move without being fixed at a position, and therefore generate heat a little to be kept at a relatively low temperature. As a result, the surface 21 (the neighborhood of the surface of the urethra) is protected from the effect of heating by the laser light 117.

Figure 2:
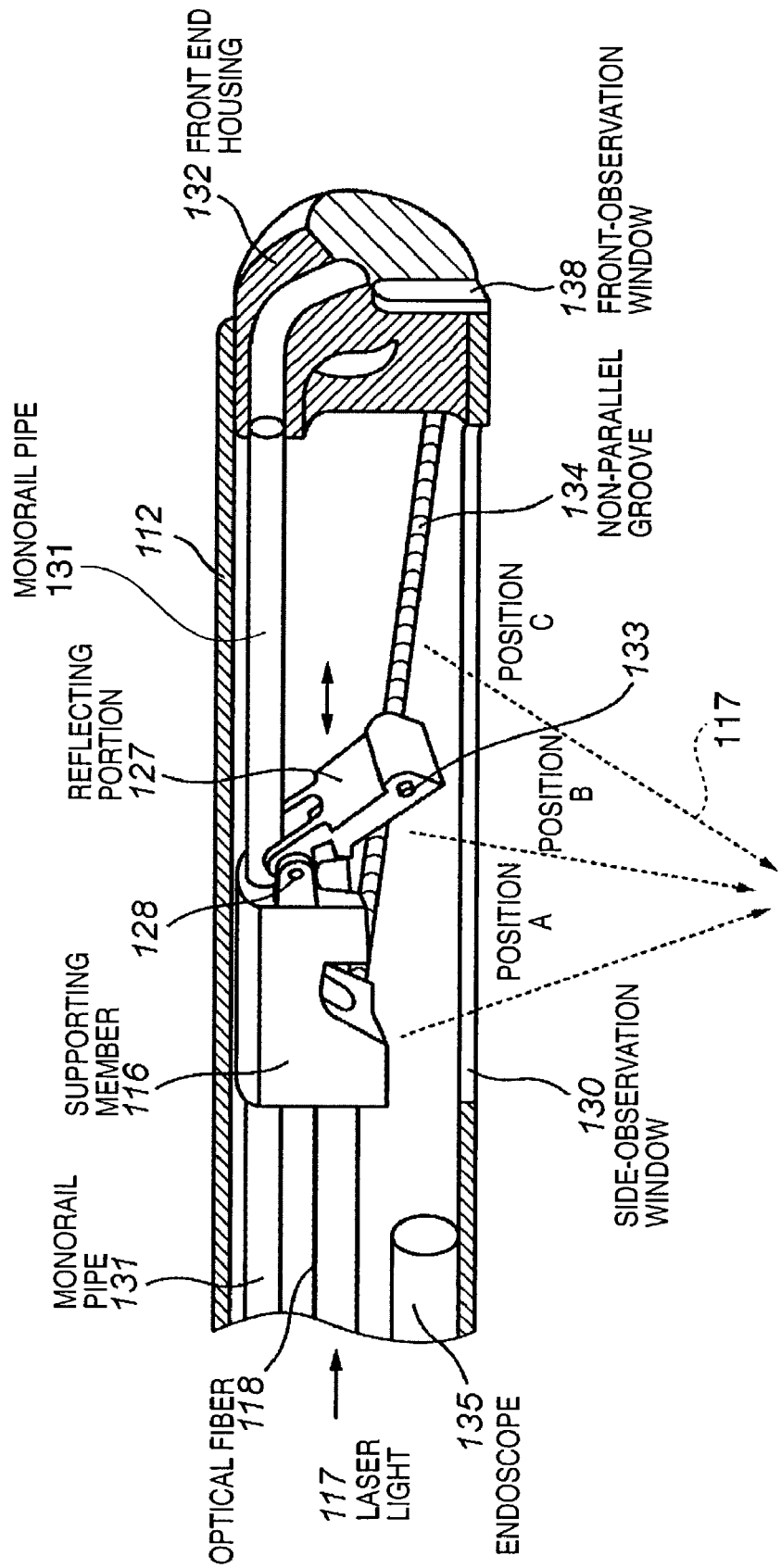
FIG. 2 is a diagram for showing a portion close to an end of an applicator according to one embodiment of the invention.

[Front End of the Applicator: FIG. 2]

FIG. 2 is a perspective view of the front end of the applicator 110.

As shown in FIG. 2, the applicator 110 has a front-end housing 132 having a front-observation window 138, the reflecting portion 127 smooth and flat, contained in the housing 112 and for reflecting the laser light 117, a supporting member 116 for holding the reflecting portion 127, a monorail pipe 131 for making the supporting member 116 movable in the longitudinal direction of the applicator 110, non-parallel grooves 134 for varying an angle of the reflecting portion 127 such that irradiation with the laser light 117 reflected by the reflecting portion 127 may be always directed toward the same site, and an endoscope 135 for observing the tissues of the living body.

The reflecting portion 127 is linked with a drive unit 150 (FIG. 1) placed at the basal end of the applicator 110 via the supporting member 116. Thus, the reciprocating motion of the reflecting portion 127 in the direction indicated by an arrow in the figure is made possible by the movement of the supporting member 116 in the longitudinal direction of the applicator 110.

The drive unit 150 (FIG. 1) has a cam mechanism (not shown) for converting a rotary motion of the motor 188 (FIG. 1) into a reciprocating motion, and thus allows the reflecting portion 127 to reciprocate in the longitudinal direction of the applicator 110 according to the rotation of the motor 188 (FIG. 1). The housing 112 is configured by a hard tube-like body having a side-observation window 130.

Figure 3:
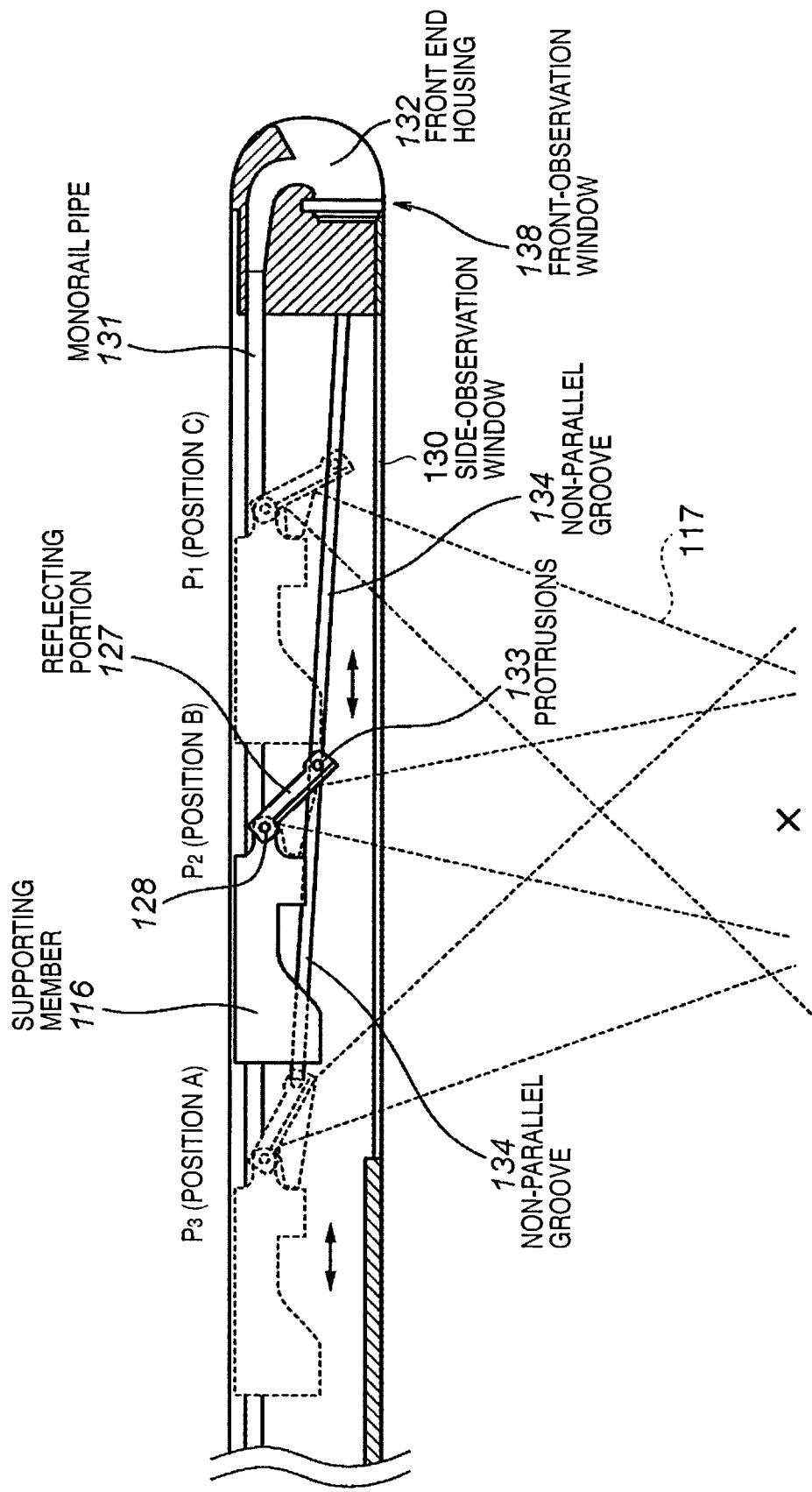
FIG. 3 is a diagram for illustrating a relation between an operation of a reflection plane of the applicator according to one embodiment of the invention and a direction of irradiation with laser light.

[Structure of the Reflecting Portion and Support Member: FIG. 3]

FIG. 3 is a cross-sectional view for illustrating structures of the reflecting portion 127 and the supporting member 116, which slide on the monorail pipe 131 of the applicator 110 described with reference to FIG. 2.

The supporting member 116 supports the reflecting portion 127. A support portion 128 is provided on one side of the reflecting portion 127, and a pair of protrusions 133 are provided on the other side. The support portion 128 is to mount the reflecting portion 127 such that it can rotate independently of the support member 128, and the support portion 128 is adaptable for changes in reflection angle of the reflecting portion 127. The protrusions 133 are fitted with the non-parallel grooves 134 arranged on the inner wall of the housing 112.

The supporting member 116 is linked with the drive unit 150 (FIG. 1) placed at the basal end of the applicator 110, and slides on the monorail pipe 131, thereby allowing the reflecting portion 127 to reciprocate in the longitudinal direction of the applicator 110. For this reason, the reflecting portion 127 can vary its angle of inclination with its movement in the axial direction based on the linkage between the supporting member 116 and the non-parallel grooves 134.

Figure 4:
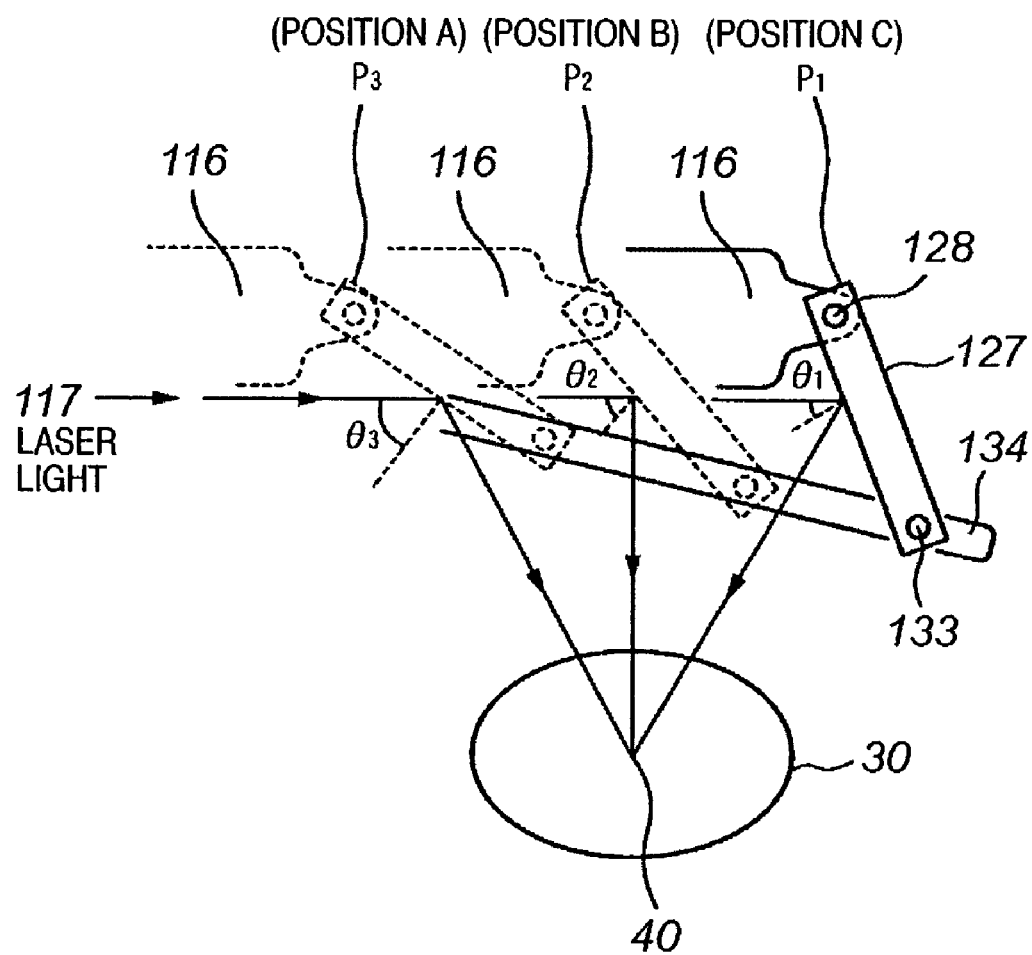
FIG. 4 is a diagram for illustrating an operation of a reflection plane and a position of an irradiation target site of a tissue of a living body on which laser light is concentrated, according to one embodiment of the invention.

[Relation Between the Reflecting Portion and Laser Light: FIG. 4]

FIG. 4 is a diagram for illustrating a relation between the movement of the reflecting portion 127 and a direction of irradiation with the laser light 117.

As shown in FIG. 4, a distance between the supporting member 116 and the non-parallel groove 134 at $P_2$ (position B) is shorter than that at $P_1$ (position C). For this reason, when the support portion 128 of the reflecting portion 127 moves from $P_1$ (position C) to $P_2$ (position B), the protrusions 133 of the reflecting portion 127 slide along the non-parallel grooves 134 and thus the angle of inclination of the reflecting portion 127 is adjusted. That is, the angle of inclination of the reflecting portion 127 with respect to the monorail pipe 131 is adjusted to become small.

Similarly, when the support portion 128 of the reflecting portion 127 moves from $P_2$ (position B) to $P_3$ (position A), the angle of inclination of the reflecting portion 127 with respect to the monorail pipe 131 is adjusted to become smaller.

On the other hand, in between $P_1$ (position C)—$P_3$ (position A), the laser light 117 reflected by the reflecting portion 127 is established to be always concentrated on the irradiation target site (target position) 40 of the target prostate gland (target site) 30. For this reason, only the irradiation target site (target point) 40 is continuously irradiated with the laser light 117, and the other tissues such as those of the surface are intermittently irradiated. Therefore, the irradiation target site 40, continuously irradiated with the laser light, generates a large amount of heat due to the irradiation and thus is heated to a desired high temperature. On the other hand, the positions other than the irradiation target site 40, such as the surface 21, intermittently irradiated with the laser light 117 generates a small amount of heat due to the irradiation, thereby being little heated. Therefore, while suppressing a rise in temperature at the portion of the surface 21, it is possible to heat only the irradiation target site 40 and the neighborhood thereof by the laser light 117 to a desired temperature.

Further, in the above description, the non-parallel grooves 134 have been described as straight lines, but they are not limited to be like straight-lines, and they may be like curved lines.

Also, the reflecting portion 127 for reflecting the laser light 117 reciprocates on the monorail pipe 131 in the longitudinal direction of the applicator 110 at a cycle of 2–10 Hz, preferably 3–6 Hz, while varying its angle.

Herein, the laser light 117 for irradiation is preferably divergent light, collimated light, or convergent light. Also, optics for converting the laser light 117 into convergent light may be provided at some midpoint in the optical path of the laser light 117. In addition, although the laser light 117 used is specifically not limited as far as it has in-the-living-body reachability, the laser light preferably has a wavelength of 750–1300 nm or 1600–1800 nm.

For example, a gas laser such as a He—Ne laser, a solid laser such as an Nd-YAG laser, and a semiconductor laser such as a GaAlAs laser are applicable to the laser light generating unit 2 for generating the laser light 117 having a wavelength above described. Also, the diameter of the inserting portion of the applicator 110, or the outer diameter of the applicator 110, is not specifically limited as far as it can be inserted into a body cavity 22. However, the outer diameter of the applicator 110 is preferable in the degree of 2–20 mm, more preferably 3–8 mm.

[Positioning Marker: FIG. 5]

FIG. 5 shows one example in which positioning markers 140 are arranged in the interior of the applicator 110.

That is, the positioning markers 140 are arranged at a front position ($M_1$), central position ($M_2$), rear position ($M_3$) and four positions ($m_1$, $m_2$, $m_3$, $m_4$) spaced an equal spacing (for example, 3 mm) between the central position ($M_2$) and the rear position ($M_3$) in the reflecting portion 127 for reflecting the laser light 117.

Herein, the front position ($M_1$) and the rear position ($M_3$) indicate the limit points of irradiation with the laser light 117 radiated toward tissues of a living body, and the front position ($M_1$) indicates the limit point of irradiation on the front end side of the inserting portion, and the rear position (M3) indicates the limit point of irradiation on the basal end side of the inserting portion.

Further, in FIG. 5, the shape of the markers is shown as lines, but arbitrary shapes (for example, points, triangles, etc.) may be used as far as doctors can identify the shapes by using an endoscope. Also, the color of the markers is not specifically limited, any color may be used as far as doctors can identify the colors by using an endoscope. Each marker may be color coded, including that the markers of the front position ($M_1$), central position ($M_2$) and rear position ($M_3$) are changed from one another in color.

Also, the number of the markers is not limited to the example described above (seven markers), but arbitrary number of the markers may be established to be arranged. Further, the spacing of markers is not limited to the example described above, but any spacing may be used as far as doctors can identify the spacing by using an endoscope. Preferably the spacing of 1–5 mm, more preferably 2–3 mm, is easy to identify.

[Other Positioning Markers: FIGS. 15A to 15C, 16A to 16C, 17]

Figure 15A:
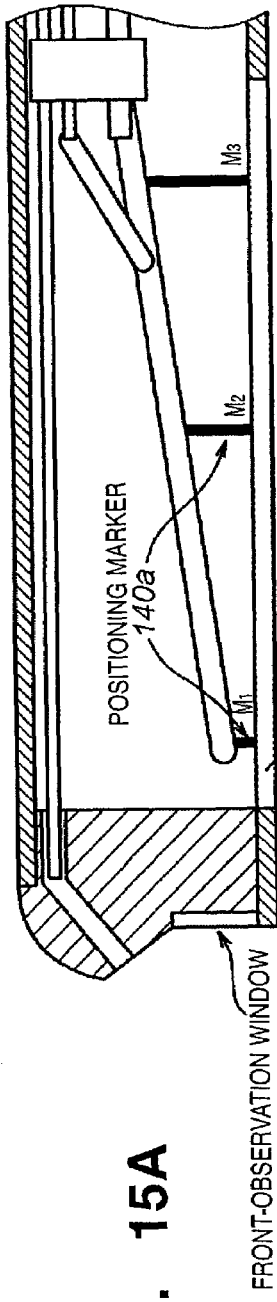
FIGS. 15A–15C are diagrams in which positioning makers of different kinds from that of FIG. 5 are arranged in an interior of the applicator according to one embodiment of the invention.

Further, the positioning markers arranged in the interior of the applicator 110 are not limited to those of FIG. 5, but for example, the positioning markers shown as examples in FIGS. 15A–17 may be used. (FIGS. 15A, 15B and 15C show the case where the same positioning marker as in FIG. 5 are arranged, for comparison.)

Figure 15B:
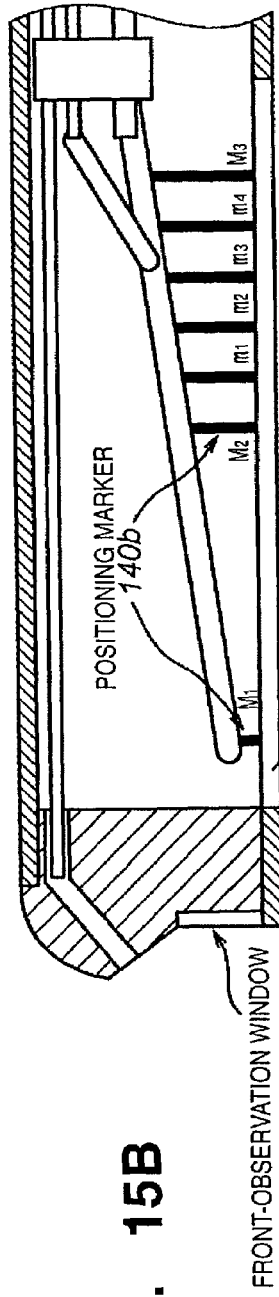
Figure 15C:
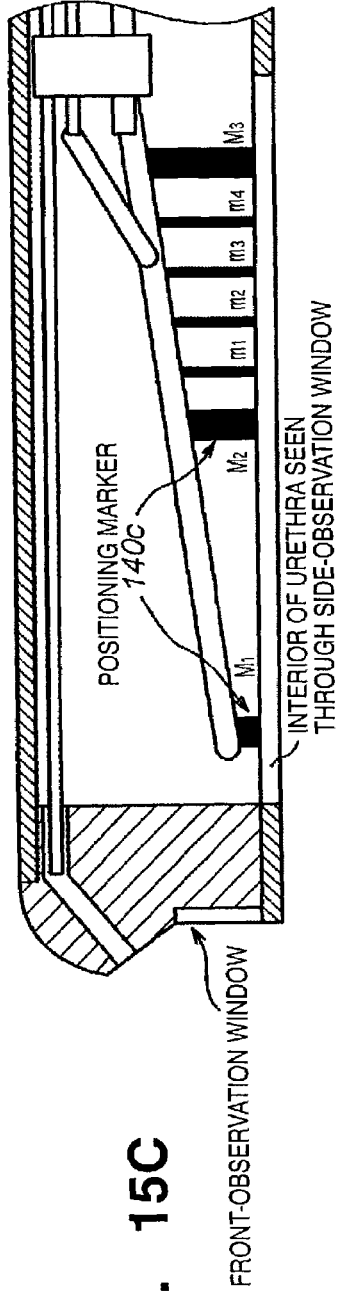

For example, positioning markers 140a shown in FIG. 15A show the case where only the markers of the front position ($M_1$), central position ($M_2$) and rear position ($M_3$) among positioning makers 140 shown in FIG. 15B are arranged in the interior of the applicator 110. Also, positioning markers 140c shown in FIG. 15C shows the case where the markers of the front position ($M_1$), central position ($M_2$) and rear position ($M_3$) among the positioning makers 140 shown in FIG. 15B are made larger.

Also, a positioning markers 140d shown in FIG. 16A shows the case where only the marker of the central position ($M_2$) among the positioning markers 140 shown in FIG. 15B is used. A positioning marker 140e shown in FIG. 16B shows the case where only the marker of the rear position ($M_3$) among the positioning markers 140 shown in FIG. 15B is used. Positioning markers 140f shown in FIG. 16C show the case where the markers of the central position ($M_2$) and rear position ($M_3$) among the positioning markers 140 shown in FIG. 15B, and four markers arranged with an equal spacing between the central position ($M_2$) and the rear position ($M_3$) are used.

Figure 17:
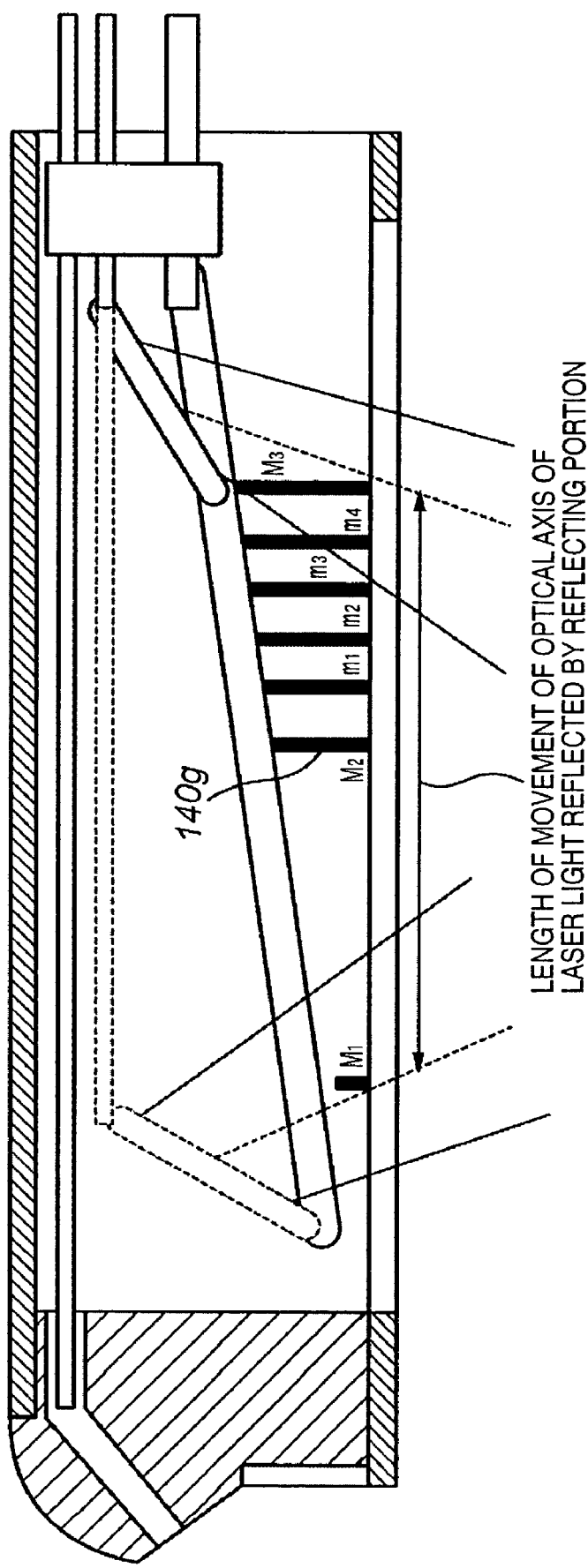
FIG. 17 is a diagram in which a positioning marker of a kind different from that of FIG. 5 is arranged in the interior of the applicator according to one embodiment of the invention, and both ends of the positioning marker shows the limits of movement of a center of the laser light.

Also, positioning markers 140g shown in FIG. 17 have the same number (seven markers) as and an arrangement similar to the positioning markers 140 shown in FIG. 15B, except that the front position ($M_1$) and the rear position ($M_3$) indicate the limit points of movement of the optical axis of the laser light 117 reflected by the reflecting portion 127 and applied to tissues of a living body.

Figure 18A:
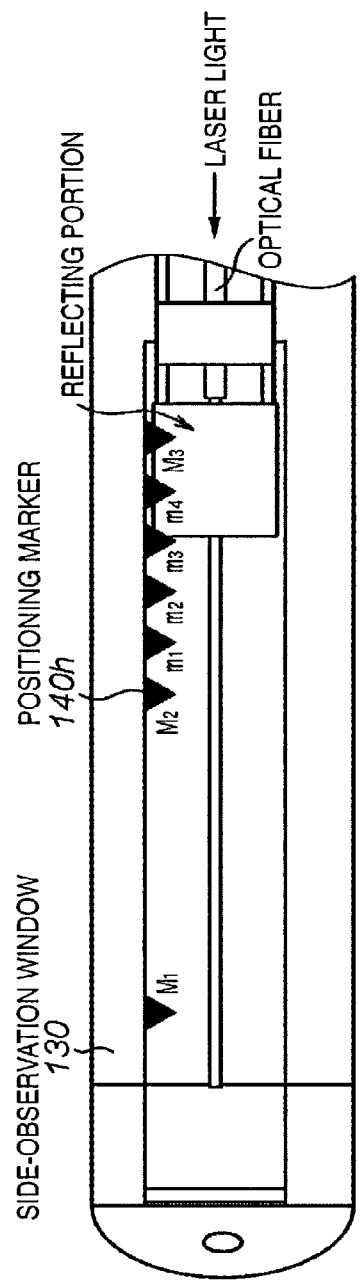
FIGS. 18A–18C are diagrams in which positioning markers of different kinds from that of FIG. 5 are arranged on a side-observation window of the applicator according to one embodiment of the invention.
Figure 18B:
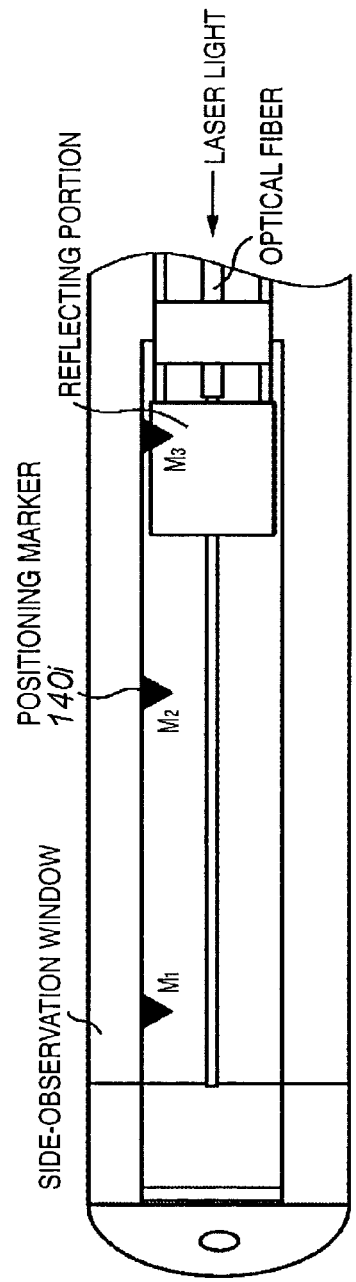
Figure 18C:
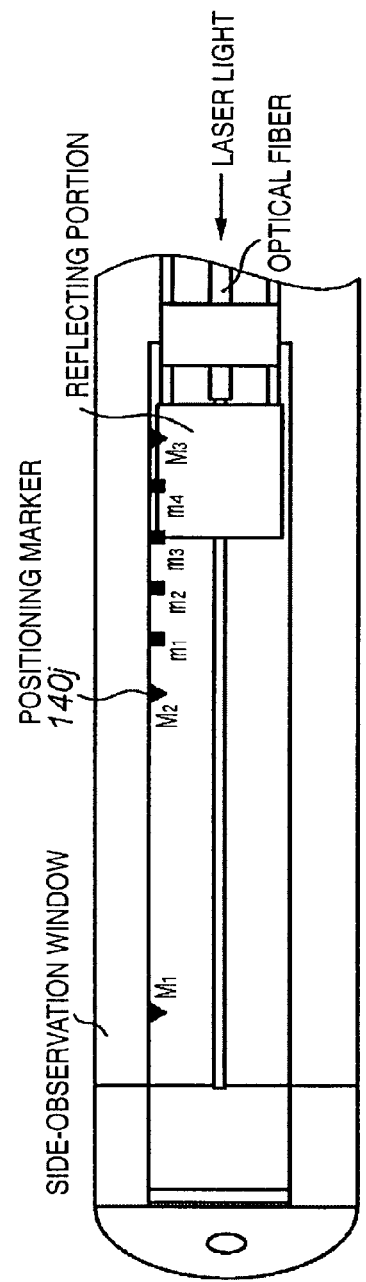

[Another Positioning Marker: FIGS. 18A, 18B and 18C]

Furthermore, the positioning markers arranged in the interior of the applicator 110 are not limited to those of FIGS. 15A–17, but for example, they may be arranged on the side-observation window 130 like one example shown in FIGS. 18A, 18B and 18C.

For example, the positioning markers 140h shown in FIG. 18A show the case where the markers arranged similarly to the arrangement ($M_1$, $M_2$, $M_3$, $m_1$, $m_2$, $m_3$, $m_4$) used in the positioning markers 140 shown in FIG. 5 are provided on the side-observation window 130.

Also, the positioning markers 140i shown in FIG. 18B show the case where only those of the front position ($M_1$), central position ($M_2$) and rear position ($M_3$) shown in FIG. 18A are used.

Also, the positioning markers 140j shown in FIG. 18C have a changed shape of the positioning markers shown in FIG. 18A.

Figure 20:
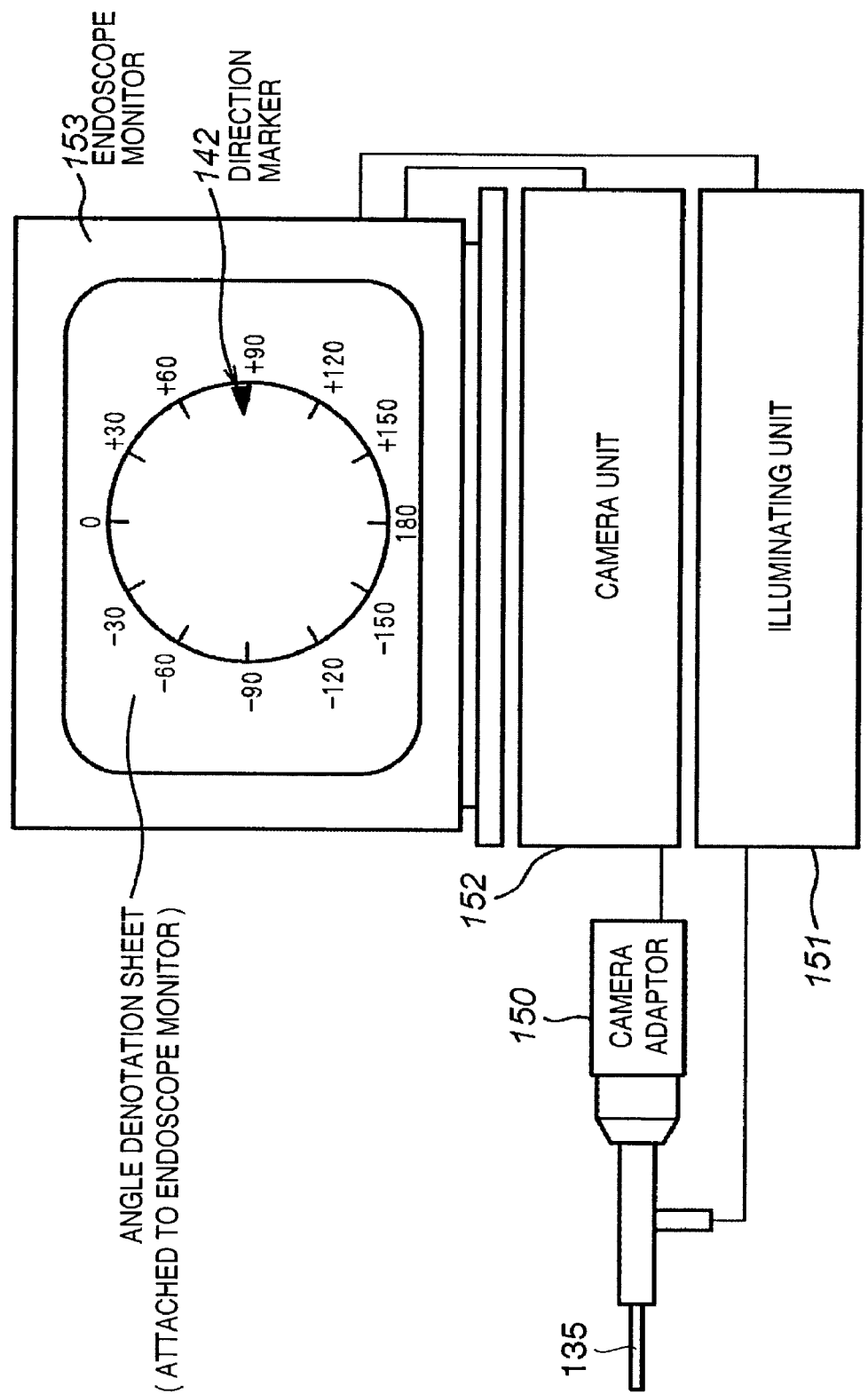
FIG. 20 is a diagram for showing a configuration of an endoscope observation system according to one embodiment of the invention and an example in which the angle denotation sheet of the endoscope is affixed on an endoscope monitor.

[Endoscope: FIG. 20]

By the way, as shown in FIG. 20, a camera adapter 150 connected to the endoscope 135 is provided at the basal end of the endoscope 135 described above, and a signal for displaying an image on an endoscope monitor 153 is designed to be sent from the camera adapter 150 to a camera unit 152.

The camera adapter 150 is connected in such a structure that the adapter will not rotate even though the endoscope 135 rotates, in order that the rotation of the endoscope 135 may be visible on the endoscope monitor 153.

An illuminating unit 151 is to apply illumination to a visual field 141 of the endoscope, and the illumination emitted from the illuminating unit 151 is transmitted to the endoscope 135 through an optical fiber or the like, and the illumination is emitted forward from the tip of the endoscope 135.

A direction marker 142 is provided in the endoscope 135, and the direction marker 142 is designed to appear at the position of reference rotation of the endoscope 135 (at six o'clock position, that is, the direction in which the side-illumination window is present when the endoscope is inserted into the inserting portion).

In the case shown in FIG. 20, the direction marker can be observed in a direction of +90°. Therefore, it can be grasped that the positioning has been done such that irradiation with energy may be directed toward the direction of +90° (three o'clock position).

Herein, the position of reference rotation is not limited to six o'clock position, but it may be twelve o'clock position or the like.

[Observation of the Positioning Maker 1: FIGS. 6A and 6B]

Next, the applicator 110 having the positioning marker 140 described with reference to FIG. 5 is inserted into a urethra 23, and further the endoscope 135 is inserted into the applicator 110 to a predetermined position. Thus, when tissues of a living body are observed by the endoscope 135 through the front-observation window 138 or the side-observation window 130 of the applicator 110, it will be described by using the examples of FIGS. 6A–FIGS. 8B how a predetermined site to be observed in the tissues of a living body (in this case, a urinary bladder, prostate gland 30, urethra 23, seminal colliculus 144, etc.) changes according to the positional relation between the applicator 110 and the front-observation window 138 or the side-observation window 130.

First, FIGS. 6A and 6B will be described.

FIG. 6A is a diagram for showing a cross-section of the applicator 110 inserted into the urethra 23, showing one example in which the endoscope 135 is inserted near to a front end of the applicator 110.

In the placement of FIG. 6A, tissues of a living body observed by endoscope 135 is only that existing within the visual field 141 of the front-observation window 138.

Further, in FIG. 6A, the endoscope 135 is in contact with the front-observation window 130, but the endoscope 135 and the front-observation window 130 may be spaced 0–3 mm apart, preferably 0–1 mm, as far as the forward-observation is permitted.

FIG. 6B is a schematic diagram for showing one example of tissue sites of a living body observed by the endoscope 135, in the state of FIG. 6A. The urethra 23 is observed in both sides (displayed by dotted lines) of the observed image and the seminal colliculas 144 is observed toward a lower position (displayed by a dotted line) of the observed image. These are the tissues of a living body observed through the front-observation window 130 and existing forward of the front end of the applicator 110.

Also, the direction marker 142 pointing the direction of irradiation with laser light is displayed at the lower part of the observed image.

[Observation of the Positioning Marker 2: FIGS. 7A and 7B]

Next, FIGS. 7A and 7B will be described.

FIG. 7A is a diagram for showing a cross-section of the applicator 110 inserted into the urethra 23, showing one example of the case in which the endoscope 135 is inserted near the central portion of the applicator 110.

In the placement of FIG. 7A, what is observed by the endoscope 135 is present within the visual field 141. That is, there are observed the tissues of a living body, which are present within the visual field 141 and observed through the front-observation window 138 and the side-observation window 130, and the interior 147 of the applicator.

FIG. 7B is a schematic diagram for showing one example of tissue sites of a living body observed by the endoscope 135 in the state of FIG. 7A. The interior of the urethra 143 observed through the front-observation window 138 is observed in the central part of the observed image (enclosed in a rectangle by dotted lines). Also, tissues of a living body 146 observed through the side-observation window 130 are observed toward a lower part (indicated by a dotted line) of the observed image, and the interior 147 of the applicator is observed in an upper portion (displayed by a dotted line) of the observed image.

In the interior 147 of the applicator, there are $M_1$ located at the front position and $M_2$ located at the central position among the positioning markers 140. Also, the direction marker 142 for pointing the direction of irradiation with laser light is displayed in the lower part of the observed image.

[Observation of the Positioning Marker 3: FIGS. 8A and 8B]

Next, FIGS. 8A and 8B will be described.

FIG. 8A is a diagram for showing the cross-section of the applicator 110 inserted into the urethra 23, showing one example of the case in which the endoscope 135 is inserted closer to the basal end of the applicator 110.

In the placement of FIG. 8A, what is observed by the endoscope 135 is present within a visual field 141. That is, there is observed the tissues of a living body, which are present within the visual field 141 and observed through the side-observation window 130, and the interior 147 of the applicator.

Also, because the front-observation window 138 is remote from the endoscope, it is impossible to observe tissues of a living body observable through the front-observation window 138. However, when an endoscope having high resolution and high illuminance of illumination is used, it is also possible to observe the tissues of a living body 146 observable through the front-observation window 138.

FIG. 8B is a schematic diagram for showing one example of tissue sites of a living body observed by the endoscope 135 in the state of FIG. 8A. The tissues 146 of a living body observed through the side-observation window 130 is observed toward a lower part (displayed by a dotted line) of the observed image. Also, the interior 147 of the applicator is observed toward an upper part (displayed by a dotted line) of the observed image.

In the interior 147 of the applicator, there are displayed $M_2$ located at the central position, $M_3$ located at the rear position and the four makers ($m_1$, $m_2$, $m_3$, $m_4$) among the positioning markers 140 and the reflecting portion 127. Also, the direction marker 142 for indicating the direction of irradiation with laser light is displayed in the lower portion of the observed image.

[Movement Mechanism of the Endoscope and the Applicator: FIGS. 9A, 9B and 9C]

Next, a movement mechanism of the above endoscope 135 and the applicator 110 will be described with reference to FIGS. 9A, 9B and 9C.

A slide lever 149 can be inserted into a basal end portion 148 and have a structure removably attached to the endoscope 135. Further, the junction portion between the slide lever 149 and the endoscope 135 is completely fastened by a fastening device such as a not-shown screw.

Also, the basal end portion 148 is provided with a not-shown hole into which the slide lever 149 is inserted, and the shape of the hole and the inserting portion of the slide lever 149 are shaped into a rectangle. Therefore, the rotation angle when the applicator 110 is rotated about the longitudinal axis thereof is equal to the rotation angle when the applicator 110 is rotated about the longitudinal axis thereof.

That is, the endoscope 135 is movable in the longitudinal direction of the applicator 110, but the endoscope 135 is configured such that it cannot rotate alone about the longitudinal axis thereof with respect to the applicator 110.

FIGS. 9A, 9B and 9C are diagrams for showing a cross-section of the applicator 110 and the basal end portion 148, showing one example where the endoscope 135 is inserted near to the front end of the applicator 110.

FIG. 9B shows the state (movement distance $L_1$) when only the applicator 110 is moved from the state of FIG. 9A toward a deep part of the urethra with the endoscope 135 fixed. This movement is performed by using the slide lever 149 provided in the basal end portion 148.

FIG. 9C shows the state (movement distance $L_2$) when only the applicator 110 is moved from the state of FIG. 9B toward a further deep part of the urethra with the endoscope 135 fixed. This movement is performed by using the slide lever 149 provided in the basal end portion 148.

As described above, when the endoscope 135 and the applicator 110 are established at a predetermined position in the urethra, they can be accurately positioned in place by using the slide lever 149 provided in the basal end portion 148.

[Determination Procedure of the Laser-Irradiated Position: FIGS. 10A–14B]

Next, with reference to FIGS. 10A–14B, the following description will be made for a procedure for determining a position to be irradiated with laser light, which position is required for doctors to use the applicator 110 and endoscope 135 described above and to perform a cure for the prostatic hypertropy using a medical energy irradiation apparatus 10.

Figure 10A:
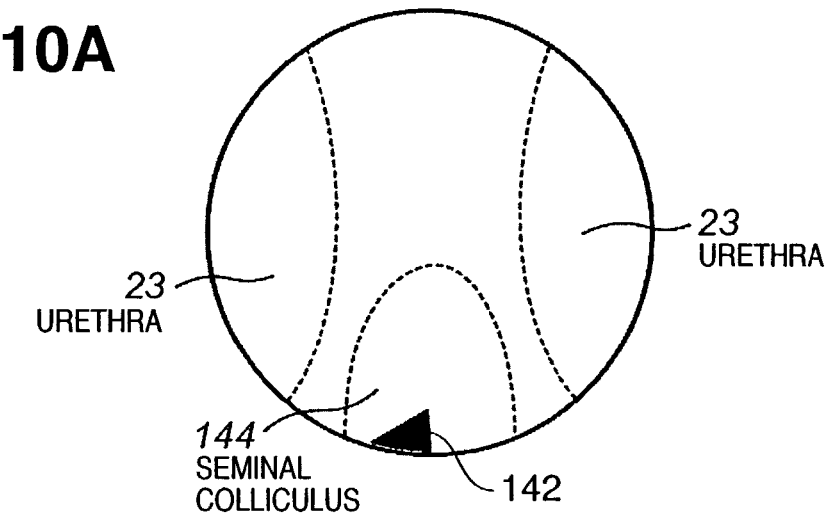
FIG. 10A is a diagram for showing an example of the tissue of a living body observed by the endoscope located at a position of FIG. 10B.
Figure 10B:
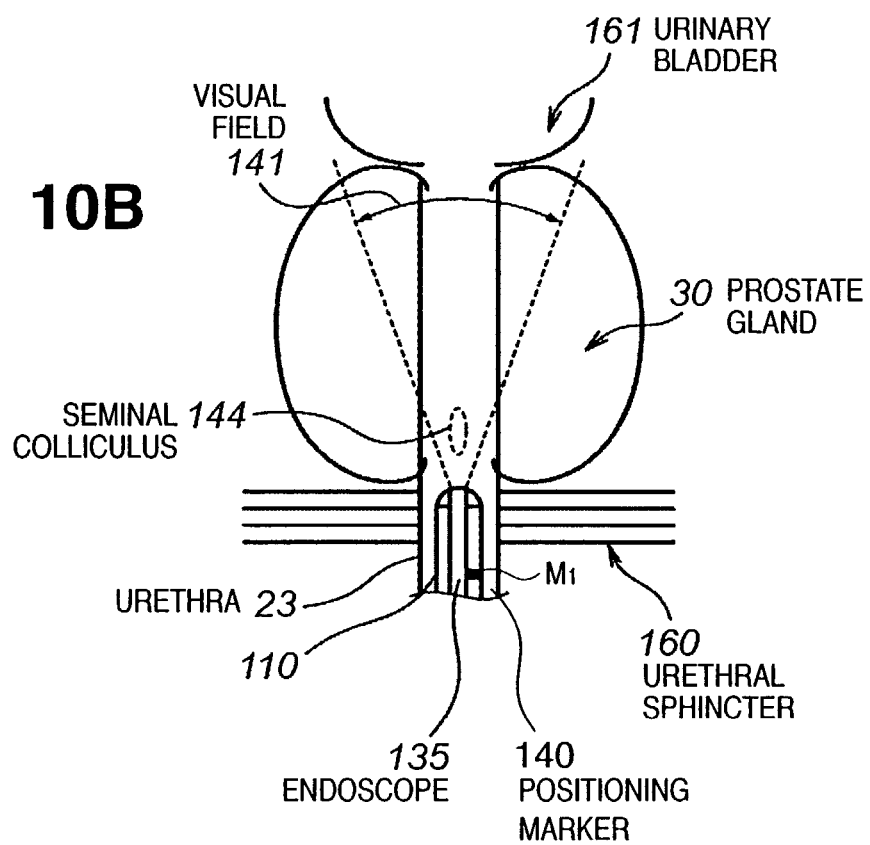
FIG. 10B is a diagram for illustrating a position where an applicator having the endoscope inserted to a front end thereof is inserted near to a urethra sphincter muscle of a urethra.

[Endoscope-Fixed Position: FIGS. 10A and 10B]

First, FIGS. 10A and 10B will be described.

Doctors insert the applicator 110 into the urethra 23 of a patient, and use the endoscope 135 to make sure the position to which the applicator has been inserted.

FIG. 10B shows a state in which the applicator 110 is inserted near to the urethral sphincter 160 in the urethra 23 with the endoscope 135 inserted to the front end of the applicator 110.

FIG. 10A is a schematic diagram for showing one example of tissue sites of a living body observed by the endoscope 135 in the state of FIG. 10B. Herein, urethra 23 are observed in both sides (displayed by dotted lines) of the observed image and the seminal colliculus 144 is observed toward a lower part of the observed-image (displayed by dotted lines). Also, the direction marker 142 pointing the direction of irradiation with laser light is displayed in the lower part of the observed image.

The doctors make sure the position of the seminal colliculus 144 by the forward observation shown in FIG. 10B obtained through the front-observation window 138. Then, while gradually inserting the applicator 110 toward a deep part of the urethra of the patients, the doctors observe tissues of a living body as occasion requires. They insert the applicator 110 to the position where the seminal colliculus 144 can be observed as shown in FIG. 10A, and then fix the endoscope at the position.

Figure 11A:
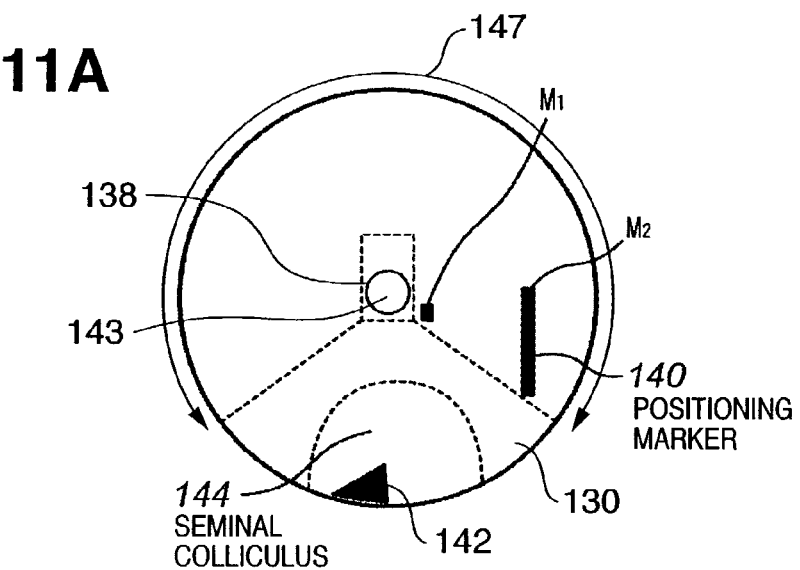
FIG. 11A is a diagram for showing an example of the tissue of a living body observed by the endoscope in the arrangement of the applicator and the endoscope as shown in FIG. 11B.
Figure 11B:
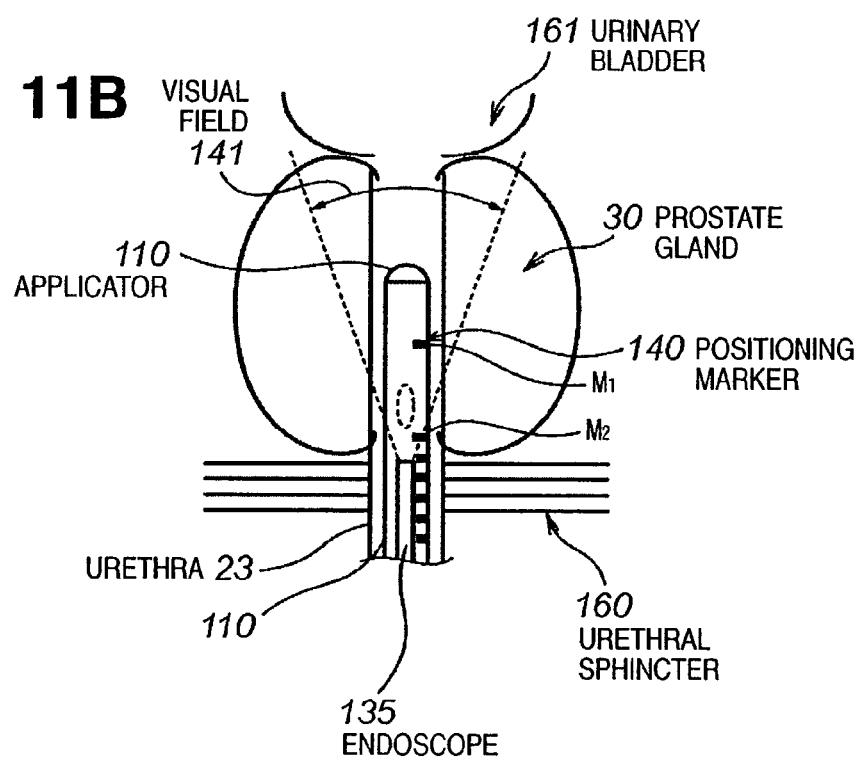
FIG. 11B is a diagram for showing a position where only the applicator is further inserted to a deeper part of the urethra, while the endoscope placed at the position of FIG. 10B remains fixed at the same position.

[Insertion of the Applicator: FIGS. 11A and 11B]

Next, FIGS. 11A and 11B will be described.

The doctors fix the endoscope 135 at the position of FIG. 10B, and then use the movement mechanism described with reference to FIGS. 9A, 9B and 9C to further insert only the applicator 110 toward the urinary bladder 161 as shown in FIG. 11B. At this time, the visual field 141 observed by the endoscope 135 gradually changes.

That is, a range observed through the front-observation window 138 gradually decreases, and ranges observed through the side-observation window 130 and in the interior of the applicator 147 gradually increase. In accompanying this, the seminal colliculus 144 becomes observable through the side-observation window 130 instead of the front-observation window 138.

FIG. 11A is a schematic diagram for showing one example of tissue sites of a living body observed by the endoscope 135 in the state of FIG. 11B. Herein, the interior 143 of the urethra observed through the front-observation window 138 is observed in the central part (enclosed in a rectangle by dotted lines) of the observed image. Also, the tissues of a living body observed through the side-observation window 130 is observed toward a lower part (displayed by a dotted line) of the observed image, and the interior of the applicator 147 is observed toward an upper part (displayed by a dotted line) of the observed image.

In the interior 147 of the applicator, there are observed $M_1$ located at the front position and $M_2$ located at the central position among the positioning markers 140. Also, the direction marker 142 for pointing the direction of irradiation with laser light is displayed in the lower part of the observed image.

By the way, in moving the applicator 110 from a state of FIGS. 10A and 10B described above to that of FIGS. 11A and 11B, as a distance between the front-observation window 138 and the side-observation window 130 is shorter, the insertion can be performed without losing sight of the seminal colliculus 144. That is, the length of slide movement of the endoscope 135, from the position where the tip of the endoscope makes contact with the front-observation window 138 to the position where the urethra can be observed at the end of the side-observation window 130, is preferably not more than 10 mm.

Figure 12A:
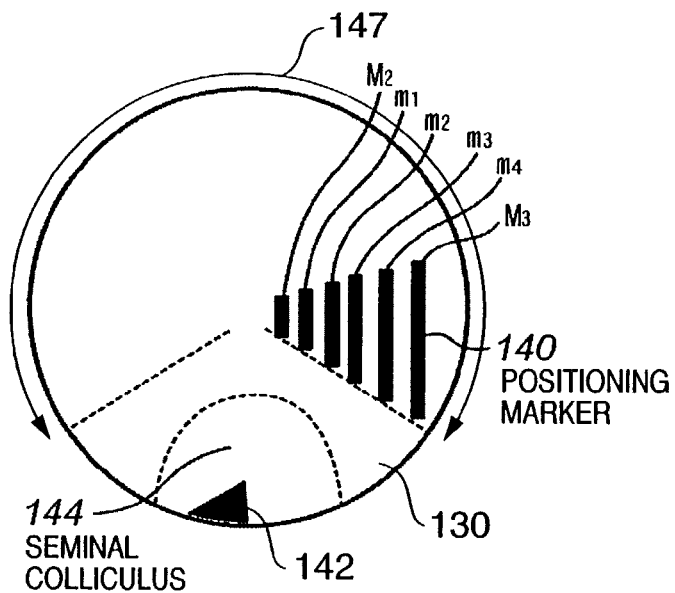
FIG. 12A is a diagram for showing an example of the tissue of a living body observed by the endoscope in the arrangement of the applicator and the endoscope of FIG. 12B.
Figure 12B:
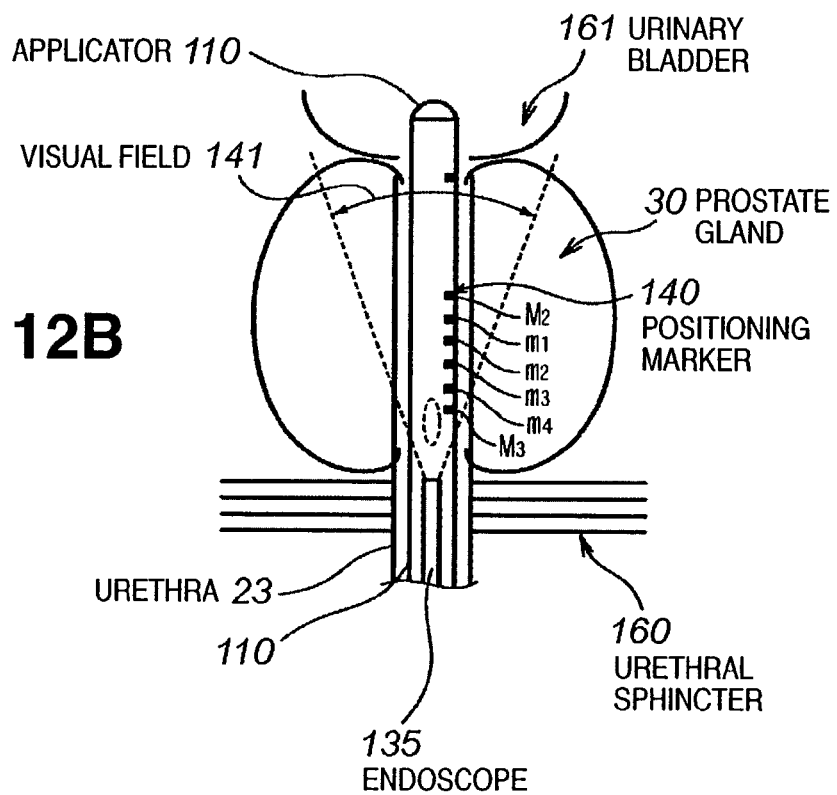
FIG. 12B is a diagram for showing the position where, only the applicator is further inserted to a deeper part of the urethra than in FIG. 11B, while the endoscope placed at the position of FIG. 11B remains fixed at the same position.

[Position Irradiated with Laser Light: FIGS. 12A and 12B]

Next, FIGS. 12A and 12B will be described.

The doctors moreover use the movement mechanism described with reference to FIGS. 9A, 9B and 9C to further insert only the applicator 110 toward the urinary bladder 161 as shown in FIG. 12B. At this time, the visual field 141 observed by the endoscope gradually changes.

That is, a range observed through the front-observation window 138 ceases to exist, resulting in only ranges observed through the side-observation window 130 and in the interior of the applicator 147.

FIG. 12A is a schematic diagram for showing one example of tissue sites of a living body observed by the endoscope 135 in the state of FIG. 12B. Herein, the tissues of a living body observed through the side-observation window 130 are observed toward a lower part (displayed by a dotted line) of the observed image, and the interior of the applicator 147 is observed toward an upper part (displayed by a dotted line) of the observed image.

In the interior 147 of the applicator, there are observed $M_2$ located at the central position, $M_3$ located at the rear position and the four markers ($m_1$, $m_2$, $m_3$, $m_4$) existing between the central position and the rear position among the positioning markers 140, the reflecting portion 127 (not shown) or the like. Further, if the resolution of the endoscope 135 is high and the illuminance of illumination is high, $M_1$ located at the front position also may be observable. Also, the direction marker 142 for pointing the direction of irradiation with laser light is displayed in the lower part of the observed image.

The doctors determine a position (for example, $m_1$) to be irradiated with laser light from the position of the seminal colliculus 144 and the position of the positioning marker 140 in the state of FIGS. 12A and 12B. Also, it can be seen from the position of the direction marker 142 that the direction of irradiation with laser light points downward.

Figure 13A:
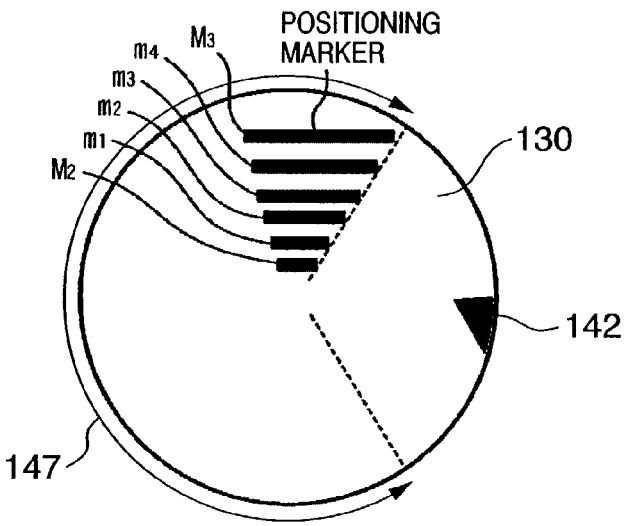
FIG. 13A is a diagram for showing an example of the tissues of a living body observed by the endoscope in the arrangement of the applicator and the endoscope of FIG. 13B.
Figure 13B:
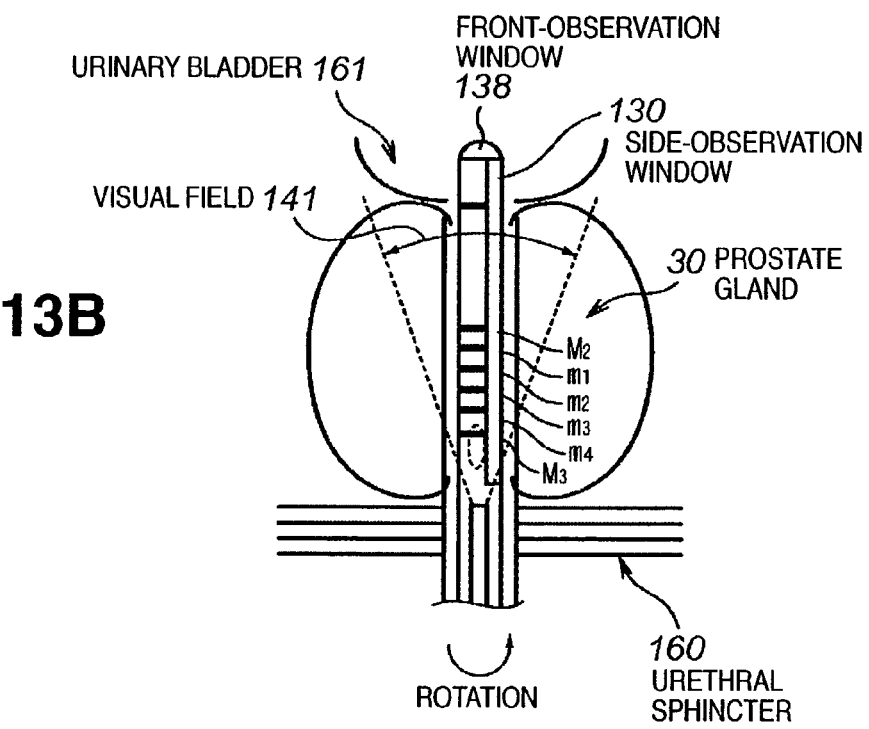
FIG. 13B is a diagram for showing a position where, the applicator placed at the position of FIG. 12B is rotated in a predetermined direction about a longitudinal axis of the applicator (as one example, rotated 90° in a counterclockwise direction)

[Laser Light Irradiation Angle: FIGS. 13A and 13B]

Next, FIGS. 13A and 13B will be described.

In the state of FIG. 12B, the direction of irradiation with laser light points downward. For example, when the left lateral lobe of the prostate gland 30 is irradiated with laser light, the doctors must change the direction of irradiation with laser light to the direction of the left lateral lobe of the prostate gland 30.

Figure 19:
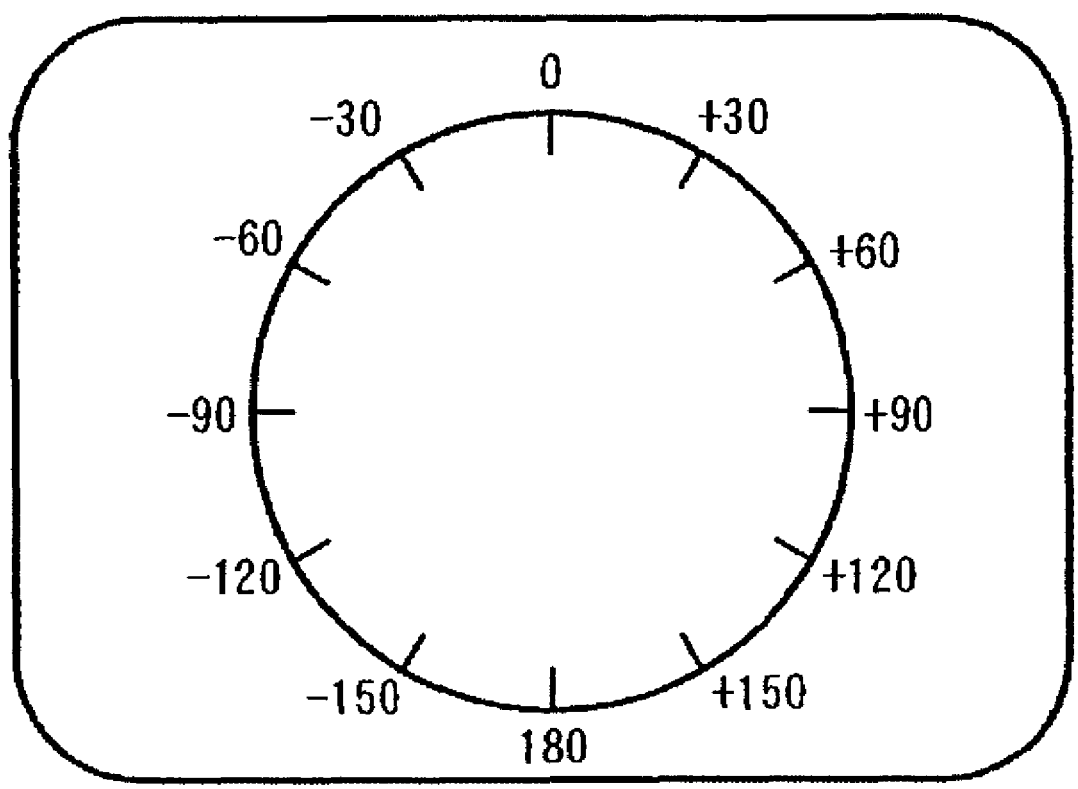
FIG. 19 is a diagram for showing an example of an angle denotation sheet of the endoscope according to one embodiment of the invention.

Therefore, the doctors rotate the basal end portion 148 (FIGS. 9A, 9B and 9C) of the applicator 110 in 90-degree angles up to the position of FIG. 13B in the position shown in FIG. 12B, and then the applicator 110 rotates, thus changing the direction of irradiation with laser light to the direction of the left lateral lobe of the prostate gland 30. At this time, because an angle denotation sheet shown in FIG. 19 is affixed on the endoscope monitor 153 (FIG. 20), the scale pointed by the direction marker 142 in the angle denotation sheet is changed from 180° to +90°.

FIG. 13A is a schematic diagram for showing one example of tissue sites of a living body observed by the endoscope 135 in the state of FIG. 13B, and this is the same diagram as that obtained at rotating FIG. 12A in 90-degree angles. Also, the direction marker 142 is observed at +90° position in the angle denotation sheet shown in FIG. 19.

Further, the rotation operation described above is one example, and the operation of rotation to the directions other than +90° is similar to that. Also, the angle denotation sheet shown in FIG. 19 is one example, the shape of scales may be a "point", but not a "line". Further, the notation of the scales may be "o'clock", but not "degree". Furthermore, the color of the scales may be arbitrary as far as they can be distinguished.

In addition, although the angle denotation sheet can be made of any material as far as it is transparent, the material is preferably a film material removably attached to the endoscope monitor. Also, the angle denotation does not need to be indicated on a sheet, but it may be on an endoscope monitor having angle denotation provided initially.

As described above, according to the operations of FIGS. 10A–13B, a position to be irradiated with laser light is determined.

Figure 14A:
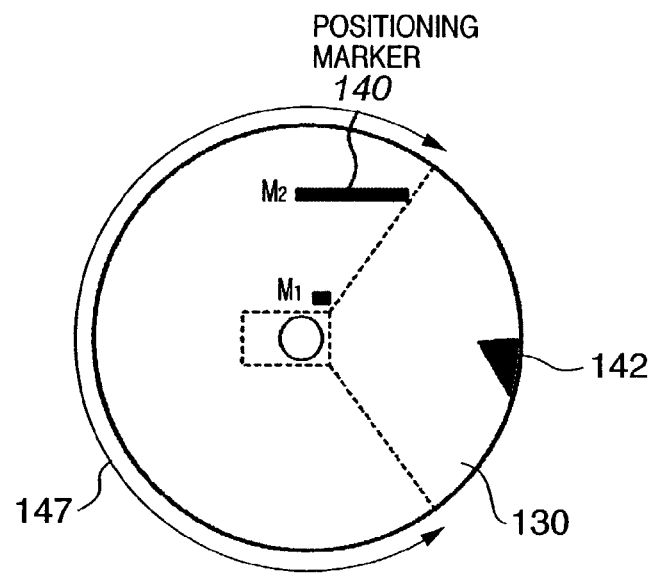
FIG. 14A is a diagram for showing an example of the tissues of a living body observed by the endoscope located at the position of FIG. 14B.
Figure 14B:
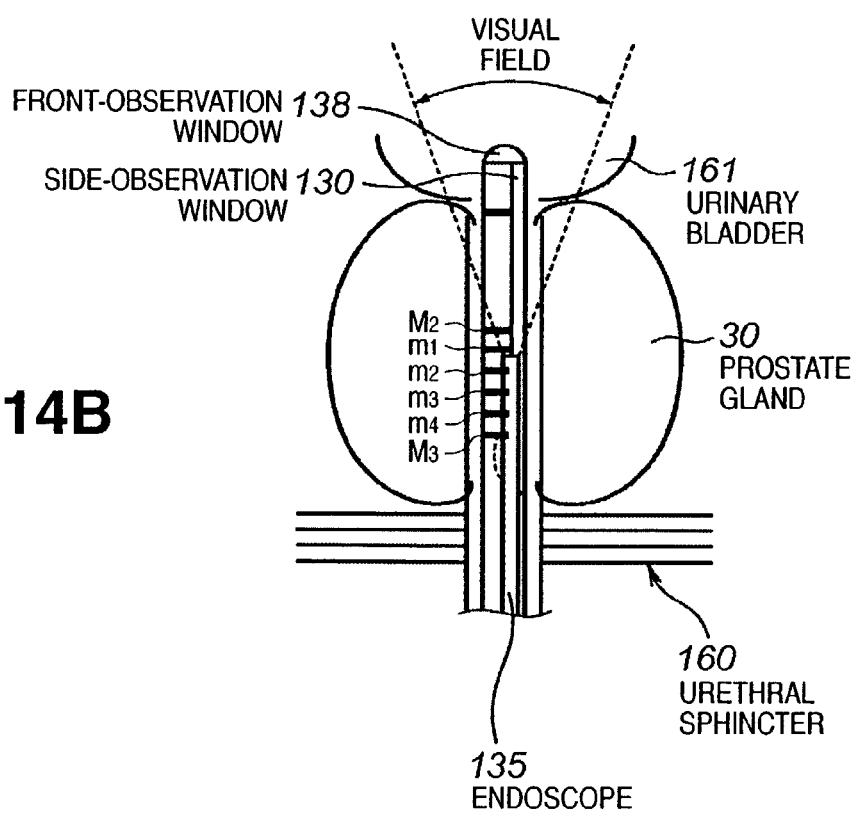
FIG. 14B is a diagram for showing a position where, the endoscope is further inserted to a deeper part of the urethra from the position of FIG. 13B, while the applicator placed at the position of FIG. 13B remains fixed at the same position.

[Laser Light Irradiation Angle: FIGS. 14A and 14B]

Next, with reference to FIGS. 14A and 14B, an ascertaining operation after determining a position to be irradiated with laser light will be described.

Although the direction of irradiation with laser light has been determined in the state of FIG. 13B, when it is wanted to check the front and back directions of the prostate gland 30 with respect to the urethra, the doctors move the endoscope 135 toward the urinary bladder 161 as shown in FIG. 14B.

FIG. 14A is a schematic diagram for showing one example of tissue sites of a living body observed by the endoscope 135 in the state of FIG. 14B. Herein, the tissues of a living body observed through the side-observation window 130 are observed in the right side part (indicated by a dotted line) of the observed image. Also, the interior 147 of the applicator is observed in the upper, lower and left side parts (displayed by dotted lines) of the observed image.

In the interior of the applicator 147, there are observed $M_1$ located at the front position and $M_2$ located at the central position among the positioning markers 140.

Therefore, the area to be irradiated with laser light can be grasped by using the positioning markers 140, and a position to be irradiated with laser light is finally determined based on the position and conditions or the like of the urethra seen through the side observation window 130.

The embodiments described above have not been described to limit the invention, but they may be variously changed within the technological principle of the invention. Also, although laser light has been exemplified and described as energy radiated toward tissues of a living body, the invention is not limited to it, and includes, for example, a microwave, radio frequency, ultrasonic wave or the like. Further, the medical energy irradiation apparatus according to the invention is preferably applied to heat curing of only prostate gland as in curing for prostatic diseases, such as the prostatic hypertropy, prostatic cancer, while decreasing damage caused by heating of normal tissues, such as a urethra and rectum, existing in the proximity of the prostate gland.

As described above, the invention can provide a medical energy irradiation apparatus permitting easy and accurate establishment of a position targeted for irradiation with energy (a site to be irradiated with energy in tissues of a living body), when doctors use the medical energy irradiation apparatus to cure prostatic hypertropy or the like.

As many apparently widely different embodiments of the present invention can be made without departing from the spirit and scope thereof, it is to be understood that the invention is not limited to the specific embodiments thereof except as defined in the claims.

What is claimed is:

1. A medical energy irradiation apparatus for generating energy and irradiating tissues of a living body with the generated energy comprising:
   an inserting portion which is inserted into the living body;
   an endoscope provided in an interior of said inserting portion and being insertable along a longitudinal direction of said inserting portion;
   an emitting portion provided in the interior of said inserting portion for irradiating tissues of the living body with the energy;
   emitting portion moving means for moving said emitting portion along the longitudinal direction of said inserting portion continuously; and
   emission angle-changing means for changing an emission angle of said emitting portion continuously such that the generated energy irradiates an irradiation target position;
   wherein said inserting portion has a side-observation window and at least one position mark arranged along the longitudinal direction in an interior of said inserting portion, said side-observation window being arranged at a side portion of said inserting portion and used for observing tissues of the living body by said endoscope and irradiating tissues of the living body with the energy by said emitting portion, said at least one position mark being used for determining the irradiation target position of tissues of the living body to be irradiated with the energy based on a position of tissues of the living body observed through said side-observing window by said endoscope and a position of said at least one position mark observed by said endoscope.

2. The medical energy irradiation apparatus according to claim 1, wherein said inserting portion has a front-observation window for permitting observation of tissues of a living body existing in front of said inserting portion.

3. The medical energy irradiation apparatus according to claim 2, wherein said observation window is arranged at the side portion of said inserting portion close to said front-observation window with said energy.

4. The medical energy irradiation apparatus according to claim 3, wherein said front-observation window and said side-observation window are arranged to have the shortest distance not more than 10 mm therebetween.

5. The medical energy irradiation apparatus according to claim 1, further comprising endoscope moving means for moving said endoscope from an entering portion of said inserting portion near to said observation window.

6. The medical energy irradiation apparatus according to claim 1, wherein said position mark is a marker and provided more than one in number.

7. The medical energy irradiation apparatus according to claim 1, wherein said position mark is arranged at a position to indicate a limit point of movement of said emitting portion.

8. The medical energy irradiation apparatus according to claim 1, wherein said endoscope further comprises an irradiation direction-identifying mark for pointing a direction of irradiation with said energy.

9. The medical energy irradiation apparatus according to claim 1, wherein when said endoscope is rotated about a longitudinal axis of said inserting portion, said endoscope further has a rotation angle-identifying mark for permitting identification of a rotation direction and a rotation angle of the rotation.

10. The medical energy irradiation apparatus according to claim 1, wherein said endoscope further comprises:
   image pickup means for picking up said tissues of a living body and said position mark; and
   display means for displaying an image picked up by said image pickup means.

11. The medical energy irradiation apparatus according to claim 1, wherein said energy is laser light.

* * * * *

UNITED STATES PATENT AND TRADEMARK OFFICE
CERTIFICATE OF CORRECTION

PATENT NO. : 7,022,118 B2
APPLICATION NO. : 10/180291
DATED : April 4, 2006
INVENTOR(S) : Shigeki Ariura et al.

It is certified that error appears in the above-identified patent and that said Letters Patent is hereby corrected as shown below:

On the Title Page of the patent; Section (*) Notice: add --This patent is subject to a Terminal Disclaimer.--

Signed and Sealed this

Twenty-seventh Day of March, 2007

JON W. DUDAS
*Director of the United States Patent and Trademark Office*